US012246098B2

(12) United States Patent
Masiz et al.

(10) Patent No.: US 12,246,098 B2
(45) Date of Patent: *Mar. 11, 2025

(54) TRANS-EPITHELIAL MEMBRANE DRUG DELIVERY SYSTEM

(71) Applicants: BioPhysics Pharma, Inc., Gloucester, MA (US); John J. Masiz, Gloucester, MA (US)

(72) Inventors: John J. Masiz, Gloucester, MA (US); Zhen Zhu, Andover, MA (US)

(73) Assignees: BioPhysics Pharma, Inc., Gloucester, MA (US); John J. Masiz, Gloucester, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/604,319

(22) Filed: Mar. 13, 2024

(65) Prior Publication Data
US 2024/0216292 A1 Jul. 4, 2024

Related U.S. Application Data

(63) Continuation-in-part of application No. 18/526,864, filed on Dec. 1, 2023, which is a continuation of
(Continued)

(51) Int. Cl.
*A61K 9/70* (2006.01)
*A61K 9/00* (2006.01)
(Continued)

(52) U.S. Cl.
CPC .......... *A61K 9/7084* (2013.01); *A61K 9/0014* (2013.01); *A61K 45/06* (2013.01); *A61K 47/18* (2013.01)

(58) Field of Classification Search
CPC .................................................. A61K 9/0014
See application file for complete search history.

(56) References Cited

U.S. PATENT DOCUMENTS 3,903,159 A 9/1975 Hughes et al.
5,460,821 A 10/1995 Masiz
(Continued)

FOREIGN PATENT DOCUMENTS

EP 1 621 192 A1 2/2006
EP 2588067 B1 10/2016
(Continued)

OTHER PUBLICATIONS

Hadgraft et al (International Journal of Pharmaceutics 200 (2000) 243â247). (Year: 2000).*
(Continued)

*Primary Examiner* — Benjamin J Packard
(74) *Attorney, Agent, or Firm* — Antoinette G Giugliano; Antoinette G Giugliano PC

(57) ABSTRACT

The present invention relates to trans-epithelial membrane delivery systems, methods and kits that include an agent to penetrate the basement membrane, a membrane of the skin and mucosa previously known to be difficult to penetrate. In particular, the formulation includes a basement membrane disruptor that reversibly denatures or cleaves molecules of the basement membrane of the epithelial membrane. The formulation of the present invention further includes having at least one penetration agent, at least one vaso-modulator, and at least one active ingredient. In an embodiment, the penetration agent includes a solvent, a lipophilic agent, a hydrophilic agent, wherein the basement membrane disruptor, the vaso-modulator, and the active ingredient pass through the outer layers of the epithelial membrane. The basement membrane disruptor allows the vaso-modulator and the active ingredient pass through the basement membrane to smooth muscle. The active ingredient, once at the smooth muscle, is delivered locally to the tissue or systemically to the blood stream.

24 Claims, 4 Drawing Sheets

Related U.S. Application Data application No. 17/884,727, filed on Aug. 10, 2022, now Pat. No. 11,865,217, which is a continuation of application No. 16/582,922, filed on Sep. 25, 2019, now Pat. No. 11,446,257.

(60) Provisional application No. 62/737,479, filed on Sep. 27, 2018.

(51) Int. Cl.
 *A61K 45/06* (2006.01)
 *A61K 47/18* (2017.01)

(56) References Cited

U.S. PATENT DOCUMENTS

| | | | |
|---|---|---|---|
| 5,645,854 A | 7/1997 | Masiz | |
| 5,853,751 A | 12/1998 | Masiz | |
| 5,922,772 A | 7/1999 | Durant | |
| 5,955,507 A | 9/1999 | Durant et al. | |
| 6,611,707 B1 | 8/2003 | Prausnitz | |
| 6,635,274 B1 | 10/2003 | Masiz et al. | |
| 6,914,051 B1 | 7/2005 | Allen | |
| 7,169,814 B2 | 1/2007 | Rothbard et al. | |
| 7,198,801 B2 | 4/2007 | Carrara et al. | |
| 7,351,743 B1 | 4/2008 | Goldin et al. | |
| 7,470,433 B2 | 12/2008 | Carrara et al. | |
| 7,687,603 B2 | 3/2010 | Zhao et al. | |
| 8,309,514 B2 | 11/2012 | Zhao et al. | |
| 8,343,486 B2 | 1/2013 | Carter et al. | |
| 8,367,122 B2 | 2/2013 | Stephens et al. | |
| 8,802,085 B2 | 8/2014 | Carter et al. | |
| 9,278,233 B2 | 3/2016 | Carter et al. | |
| 9,427,419 B2 | 8/2016 | De La Torre | |
| 9,566,256 B2 | 2/2017 | Carter et al. | |
| 9,642,912 B2 | 5/2017 | Kisak | |
| 9,855,212 B2 | 1/2018 | Cozean et al. | |
| 10,322,077 B2 | 6/2019 | Carter et al. | |
| 10,624,867 B2 | 4/2020 | Varadi et al. | |
| 11,446,257 B2 | 9/2022 | Masiz | |
| 2002/0004065 A1 | 1/2002 | Kanios | |
| 2003/0133969 A1 | 7/2003 | Bergeron | |
| 2003/0185788 A1 | 10/2003 | Bothbard et al. | |
| 2003/0219417 A1* | 11/2003 | Wolfinburger, Jr. | A61L 27/507 |
| | | | 424/93.7 |
| 2004/0115135 A1 | 6/2004 | Quay | |
| 2006/0062836 A1 | 3/2006 | Carter | |
| 2007/0072802 A1 | 3/2007 | Zhao et al. | |
| 2007/0078094 A1 | 4/2007 | Zhao et al. | |
| 2007/0166361 A1 | 7/2007 | Carrara et al. | |
| 2007/0185216 A1 | 8/2007 | Snyder | |
| 2008/0319092 A1 | 12/2008 | Singh | |
| 2009/0214504 A1 | 8/2009 | Carter et al. | |
| 2009/0311200 A1 | 12/2009 | Lambert et al. | |
| 2010/0003353 A1 | 1/2010 | Stephens et al. | |
| 2010/0076035 A1 | 3/2010 | Carter | |
| 2010/0145256 A1 | 6/2010 | Carter et al. | |
| 2010/0160210 A1 | 6/2010 | Zhao et al. | |
| 2013/0245538 A1 | 9/2013 | Carter et al. | |
| 2013/0273019 A1 | 10/2013 | Carter et al. | |
| 2014/0199741 A1 | 7/2014 | Carey | |
| 2014/0377192 A1 | 12/2014 | Schaeffer-Korbylo et al. | |
| 2015/0320710 A1 | 11/2015 | Holubec | |
| 2016/0058725 A1 | 3/2016 | Carter | |
| 2016/0128957 A1 | 5/2016 | Carter et al. | |
| 2016/0129116 A1 | 5/2016 | Carter et al. | |
| 2016/0213586 A1 | 7/2016 | Carter et al. | |
| 2016/0235846 A1 | 8/2016 | Carter et al. | |
| 2017/0095433 A1 | 4/2017 | Carter et al. | |
| 2017/0232210 A1 | 8/2017 | Boeckl | |
| 2017/0239173 A1 | 8/2017 | Obae | |
| 2018/0036226 A1 | 2/2018 | Rutolo, Jr. | |
| 2018/0319825 A1 | 11/2018 | McKinley et al. | |
| 2018/0325851 A1 | 11/2018 | Varadi et al. | |
| 2020/0101025 A1 | 4/2020 | Masiz | |
| 2021/0259951 A1 | 8/2021 | Masiz | |

FOREIGN PATENT DOCUMENTS

| | | |
|---|---|---|
| WO | WO1995020950 A1 | 8/1995 |
| WO | WO1997013482 A1 | 4/1997 |
| WO | WO2003049772 A2 | 6/2003 |
| WO | WO 95/00088 | 1/2005 |
| WO | WO2010034019 A1 | 3/2010 |
| WO | WO2010065922 A2 | 6/2010 |
| WO | WO2018213071 A1 | 11/2018 |
| WO | WO2020069013 A1 | 4/2020 |

OTHER PUBLICATIONS

"Chaotropic agent" Wikipedia Nov. 26, 2019 (Nov. 26, 2019), pp. 1-2, XP055660163, Retrieved from the Internet: URL:https:;en.wikipedia.orgjwiki/Chaotropic agent, [retrieved on Jan. 21, 2020.
International Search Report and Written Opinion, PCT application No. PCT/US2019/053000, mailed Feb. 3, 2020.
Park, Alice, "Scientists Have Discovered a New Organ in the Human Body. What is the Interstitium?" *Time Magazine*, Mar. 28, 2018 (downloaded Aug. 28, 2019).
International Preliminary Report on Patentability and Written Opinion, PCT application No. PCT/US2019/053000, mailed Apr. 8, 2021.
Sethi, Anish, et al., "Moisturizers: The Slipper Road" *Indian J Dermatol* May-Jun. 61(3): 279-287 (2016).
C W Lynde, "Moisturizers: what they are and how they work" Abstract Skin Therapy Lett Dec 6(13): 3-5 (2001) https://pubmed.ncbi.nlm.nih.gov/11813097/ downloaded May 19, 2021.
"Urea" Wikipedia https://en.wikipedia.org/wiki/Urea [retrieved May 19, 2021].
Bennion, Brian J. et al., "The Molecular Basis for the Chemical Denaturation of Proteins by Urea" PNAS 100 (9): 5142-5147 (Apr. 29, 2003).
"Urea-containing cream" Wikipedia https://en.wikipedia.org/wiki/Urea-containing_cream [retrieved May 19, 2021].
"Guanidine" Drugs.com https://www.drugs.com/pro/guanidine.html [retrieved Jan. 21, 2022].
International Search Report and Written Opinion, PCT application No. PCT/US2021/018318, mailed Jun. 4, 2021.
Rossano Rocco et al.: "What Are the Proteolytic Enzymes of Honey and What They Do Tell Us? A Fingerprint Analysis by 2-D Zymography of Unifloral Honeys" *PLOS One*, vol. 7, No. 11: p. e49164, Nov. 7, 2012.
Juergens U.: "Anti-inflammatory Properties of the Monoterpene 1.8-cineole: Current Evidence for Co-medication in Inflammatory Airway Diseases" *Drug Research*, vol. 64, No. 12, 15:638-646, May 2014.
PubChem Eucalyptol (Compound), Section 11.2.1First Aid https://pubchem.ncbi.nlm.nih.gov/compound/Eucalyptol#section=First-Aid-Measures [retrieved Nov. 21, 2022].

* cited by examiner

```
┌─────────────────────────────────────────────┐
│ Provide a formulation having at least one   │
│ penetration agent, at least one basement    │
│ membrane disruptor and a delivery package   │
│ comprising a vaso-modulator and active      │
│ ingredient                                  │
│                   102                       │
└─────────────────────────────────────────────┘
                      │
                      ▼
┌─────────────────────────────────────────────┐
│ Apply formulation to or within epithelial   │
│ membrane (e.g., skin or mucosa)             │
│                   104                       │
└─────────────────────────────────────────────┘
                      │
                      ▼
┌─────────────────────────────────────────────┐
│ Penetration agent allows for passage of a   │
│ basement membrane disruptor and a           │
│ delivery package to basement membrane       │
│                   106                       │
└─────────────────────────────────────────────┘
                      │
                      ▼
┌─────────────────────────────────────────────┐
│ Basement membrane disrupter induces         │
│ reversible denaturing or cleaving of the    │
│ molecules in basement membrane to allow     │
│ for passage of delivery package to smooth   │
│ muscle                                      │
│                   108                       │
└─────────────────────────────────────────────┘
                      │
                      ▼
┌─────────────────────────────────────────────┐
│ Vaso-modulator and active ingredient of the │
│ delivery package contacts the smooth muscle │
│ and vaso-modulator causes a fluid dynamic   │
│ event to allow delivery of active ingredient│
│ to local tissue or system circulation

… # TRANS-EPITHELIAL MEMBRANE DRUG DELIVERY SYSTEM

RELATED APPLICATIONS

This application is a Continuation-In-Part of U.S. application Ser. No. 18/526,864, entitled, "Transdermal Drug Delivery System" by John J. Masiz et al., filed Dec. 1, 2023, which is a continuation of U.S. application Ser. No. 17/884,727, now patent Ser. No. 11/865,217, issued Jan. 9, 2024, entitled, "Transdermal Drug Delivery System" by John J. Masiz et al., filed Aug. 10, 2022, which is a continuation of U.S. application Ser. No. 16/582,922, now patent Ser. No. 11/446,257, issued Sep. 20, 2022, entitled, "Transdermal Drug Delivery System" by John J. Masiz et al., filed Sep. 25, 2019, which claims the benefit of U.S. Provisional Application No. 62/737,479, entitled, "Transdermal Drug Delivery System" by John J. Masiz, filed Sep. 27, 2018. The entire teachings of the above applications are incorporated herein by reference.

BACKGROUND OF THE INVENTION

The efficient delivery of drugs or active pharmaceutical agents has long been one of the goals of the pharmaceutical community. Oral delivery of medications involves gastro-intestinal impact, first pass liver effect, and inter-gut, and drug-to-drug interactions.

Historically, the success of transdermal or transmucosal delivery technologies has often been limited. The first successful class of transdermal technology consisted of the patch. Patch technology is a primitive technology using a band aid like device to hold a drug in contact with the skin. The premise is that with osmosis, the drug will passively penetrate into the skin, through the skin and then migrate into general circulation. Patch technology has generally been somewhat successful in delivering a few compounds that, among other characteristics, have a high log-p value, small Dalton weight, and a linear molecular structure with flexible molecular bonds. Currently, there are only about 15 or so drugs that meet these criteria. These are drug compounds such as nicotine, estrogen, testosterone, scopolamine, fentanyl, diclofenac, etc. At this time, about 90% or more of the pharmacopeia cannot be delivered by patch technology including the newly developed iontophoretic and microneedle patches.

Also, with respect to transmucosal delivery technologies, success has often been limited. Mucosal delivery systems have included patches, films wafers, emulsions, pastes and sprays. However, these systems have had some success but with only a few drugs. Generally, the few drugs that successfully moved through the mucosal tissue were compounds with a high log-P value, small molecular weight and a linear molecular structure that allowed for passive transmucosal penetration.

Accordingly, a need exists for trans-epithelial membrane delivery systems and methods that provide delivery of a larger variety of pharmaceutical agents and to do so in effective amounts with the convenience of traditional pill delivery. A further need exists for an improved transepithelial membrane delivery system that provides more efficient delivery of the active ingredient and to do so systemically or to targeted tissue with a faster onset of action. Such an improved trans-epithelial membrane delivery system would also avoid unwanted effects from oral delivery of medications.

SUMMARY OF THE INVENTION

Due to problems with oral delivery, research for the present invention has focused on developing a trans-epithelial delivery method of active drugs that maintain both the convenience of oral delivery while eliminating the side effects and problems associated with pills and inter-gut delivery.

The present invention relates to a formulation for trans-epithelial membrane (e.g., transdermal or transmucosal) delivery of an active ingredient to a mammal (e.g., human or animal), wherein the mammal has a body surface that comprises an epithelial membrane. For cutaneous tissue such as skin, the trans-epithelial delivery formulation passes through the skin layers of a stratum corneum, an epidermis, and a basement membrane, to the dermis and/or smooth muscle. For mucosa surface, the trans-epithelial delivery formulation passes through the mucus, a stratified squamous epithelial layer, a basement membrane, to the lamina propria and smooth muscle. In an embodiment, the formulation includes a first penetration agent comprising a digestive enzyme or a proteolytic agent (e.g., acetylcysteine, N-acetylcysteine, L-cysteine, ambroxol, bromhexine, carbocisteine, erdosteine, mecysteine, dornase alfa, althea extract, Marshmallow root, bromelain, thyme, salt water, eucalyptol, rosemary extract, cineole, peppermint, frankincense, oregano, bergamot, nutmeg, cypress, camphene, geranium, pelargonium sidoide, cinnamon, lemon, citrus, d-limonene, l-limonene, lavender, lemon grass, chamomile, and basil) The formulation can further include a second penetration agent that includes a solvent, a lipophilic agent, a hydrophilic agent, a fatty acid or a combination thereof). In an embodiment, the trans-epithelial formulation has both a first penetration agent and a second penetration agent. In another embodiment, the trans-epithelial formulation has one or more of the first penetration agent or one or more of the second penetration agent, or both. The inventive formulation further includes at least one basement membrane disruptor that reversibly denatures or cleaves molecules in the basement membrane; at least one vaso-modulator; and at least one active ingredient. The inventive formulation allows for penetration of the active ingredient to the smooth muscle. In an aspect, the body surface for use with the inventive formulation includes skin, mucosal membranes including oral mucosa (e.g., tongue, cheek, buccal pouch), vaginal mucosa, anal mucosa, throat mucosa, nasal mucosa, or ocular tissue, tracheal mucosa, lung tissue, nail surfaces (e.g., fingernail surface or toenail surface) or any combination thereof.

The penetration agent of the present invention, for example, allows the basement membrane disruptor, the vaso-modulator, and the active ingredient to pass through the epithelial layers to the smooth muscle. A first penetration agent includes acetylcysteine, N-acetylcysteine, L-cysteine, ambroxol, bromhexine, carbocisteine, erdosteine, mecysteine, dornase alfa., althea extract, Marshmallow root, bromelain, thyme, salt water, eucalyptol, rosemary extract, cineole, peppermint, frankincense, oregano, bergamot, nutmeg, cypress, camphene, geranium, pelargonium sidoide, cinnamon, lemon, citrus, d-limonene (citrus oils) or l-Limonenes (mint oils), lavender, lemon grass, chamomile, and basil. The second penetration agent includes solvents such as one or more nonpolar solvents (e.g., carbon tetrachloride (CCl4), benzene (C6H6), diethyl ether(CH3CH2OCH2CH3), hexane(CH3(CH2)4CH3, methylene chloride(CH2Cl2), toluene and a combination thereof), one or more polar aprotic solvents (e.g., propylene carbonate, acetone ((CH3)

2C=O), ethyl acetate (CH3CO2CH2CH3), dimethyl sulfoxide ((CH3)2SO) ("DMSO"), acetonitrile (CH3CN), dimethylformamide((CH3)2NC(O)H), and a combination thereof), one or more polar protic solvents (e.g., water (H—OH), isopropanol, acetic acid (CH3CO—OH), methanol (CH3-OH), ethanol (CH3CH2-OH), n-propanol (CH3CH2CH2-OH, n-butanol (CH3CH2CH2CH2-OH and a combination thereof), one or more limonenes (e.g., D-limonene, L-Limonenes and a combination thereof), lipophilic agent, or a fatty acid (e.g., linoleic acids, linolenic acids, oleic acids, stearic acids, and myristic acids, phospholipids (e.g., phosphatidylcholine, phosphatidylethanolamine, phosphatidylserine, and a combination thereof).

The formulation of the present invention includes basement membrane disruptor that allows the vaso-modulator and the active ingredient pass through the basement membrane. In an embodiment (e.g., when applying the formulation to skin or dermal surface), basement membrane disruptors used in the present invention include, for example, one or more chaotropic agents, or one or more other agents that allow for reversibly denaturing and permeability of the basement membrane proteins. Examples of a basement membrane disruptor include guanidine hydrochloride, a guanidine salt, guanidine analogs, guanidine conjugates, or any combination thereof. In another embodiment (e.g., when applying the formulation to a mucosal surface), basement membrane disruptors used in the present invention include, for example, digestive enzymes, proteases or both. Examples of a basement membrane disrupter include a serine protease, a cysteine protease, a threonine protease, an aspartic protease, a glutamic protease, a metalloprotease, an asparagine peptide lyase, a glucanase an amyl glucosidase, an alpha-amylase, an amylase, an alpha-glucanase, a beta-glucanase, a glactomannase, a hemicellulase, an acid protease, an alkaline protease, a cellulase I, a cellulase II, a lipase, a lactase, a serratio peptidase, an exo-oeptidase, an endo-peptidase, a betaine, a maltase, an ox bile extract, a phytase, a pancreatin, a pepsin, a protease I-IV, a pullulanase, sucrase, a protease invertase, a pectinase, Chymotrypsin A, α-trypsin, and β-trypsin, papain, papaya, apple pectin, ginger, turmeric bromelain, pineapple, peppermint, or a combination thereof. In an embodiment, digestive enzymes and proteases for use as a basement membrane disrupter include e.g., a lipase, a lactase, an ox bile extract, a phytase, a pancreatin, a pepsin, Chymotrypsin A, α-trypsin, and β-trypsin, papain, papaya, bromelain, pineapple, or a combination thereof.

The formulation of the present invention includes a vaso-modulator that encompasses a vasodilator or vasoconstrictor. In an embodiment, the vasodilator allows for the active ingredient to be delivered systemically or to local tissue. Examples of vasodilators include amrinone, arginine, bamethan sulphate, bencyclane fumarate, benfurodil hemisuccinate, benzyl nicotinate, buflomedil hydrochloride, buphenine hydrochloride, butalamine hydrochloride, cetiedil citrate, ciclonicate, cinepazide maleate, cyclandelate, di isopropylammonium dichloroacetate, ethyl nicotinate, heproni-cate, hexyl nicotinate, ifenprodil tartrate, inositol nicotinate, isoxsuprine hydrochloride, kallidinogenase, methyl nicotinate, naftidrofuryl oxalate, nicametate citrate, niceritrol, nicoboxil, nicofuranose, nicotinyl alcohol, nicotinyl alcohol tartrate, nitric oxide, nonivamide, oxpentifylline, papaverine, papaveroline, pentifylline, peroxynitrite, pinacidil, pipratecol, propentofyltine, raubasine, suloctidil, teasuprine, thymoxamine hydrochloride, tocopherol nicotinate, tolazoline, papaverine, xanthinol nicotinate, diazoxide, hydralazine, minoxidil, and sodium nitroprusside, clonidine, quanaberz, methyl dopa, alpha adrenoceptor, indoramin, phenoxybenzamine, phentolamine, prazosin, PDE-5 inhibitors, sildenafil, tadalafil, adrenergic neuron blocking agents, bedmidine, debrisoquine, guanethidine, ACE inhibitors, benazepril, captopril, cilazapril, enalapril, fosinopril, lisinopril, perindopril, quinapril, ramipril, ganglion blocking agents, pentolinium, trimetaphan, calcium channel blockers, amlodipine, diltiazem, felodipine, isradipine, nicardipine, nifedipine, nimodipine, verapamil, prostaglandins, prostacyclin, thrombuxane A2, leukotrienes, PGA, PGA1, PGA2, PGE1, PGE2, PGD, PGG, PGH, angiotensin II analogs, saralasin, nitroglycerin, labetalol, thrazide, isosorbide dinitrate, pentaerythritol tetranitrate, digitalis, hydralazine, diazoxide, sodium nitroprusside, and any combination thereof.

In the case in which the vaso-modulator used in the present invention is a vasoconstrictor, the active ingredient is delivered to the dermis. In an embodiment, vasoconstrictors used with the inventive formula of the present invention encompass adenosine triphosphate, amphetamine, antazoline, asymmetric dimethylarginine, cocaine, dopamine, endothelin, ephedrine, epinephrine, ergine, hydroxyamphetamine, isoproterenol, levonordefrin, metaraminol, methamphetamine, methoxamine, methylphenidate, neuropeptide Y, naphazoline, norepinephrine, oxymetazoline, phenylephrine, pseudoephedrine, tetrahydozoline, thromboxane, tramazoline, tyramine, and any combination thereof.

The trans-epithelial membrane delivery formulation or system of the present invention can deliver a wide variety of active ingredients. Active ingredients can be used to treat a number of diseases, disorders, or conditions including musculoskeletal disease, vascular disease, neurological diseases, viral, bacterial or parasitic disease, blood disease, skin disease, autoimmune diseases, organ disease, pain, and others. Accordingly, active ingredients of pharmaceuticals used to treat these diseases can be used in the trans-epithelial membrane delivery system of the present invention. Examples of active ingredients include acetaminophen, acetohydoxamic acid, acetophenazine, acyclovir, albuterol, allopurinol, amiloride, amoxicillin, amphetamine, ampicillin, antisense polymers, atenolol, baclofen, beclomethasone, benfotiamine, betamethasone, budesonide, bumetanide, butorphanol, carbamazepine, carphenazine, celacoxhib, cefuroxime, cephradine, chloramphenicol, chlorothiazide, chlorzoxazone, cinoxacin, clorazepate, cloxacillin, cyclacillin, dapsone, dicloxacillin, diethylstilbestrol, dopamine, doxorubicin, erythropoietin, estradiol, fenoprofen, gabapentin, human growth hormone, hydralazine, hydrochlorothiazide, ibuprofen, indomethacin, insulin, isoproterenol, ketoprofen, levodopa, levothyroxine, meclofenamate, melphalan, metformin methyl salicylate, metronidazole, minoxidil, morphine, nadolol, nalidixic acid, naproxen, nomifensine, norfloxacin, oxaprozin, oxycontin, paramethasone, peptide fragments, perphenazine, phenylpropanolamine, pregabalin, probenecid, quinethazone, ritodrine, scopolamine, serotonin, sildenafil, tadalafil, terbutaline, terfenadine, tocainide, terbinafine, triamterene, riamterine, trimethoprim, valacyclovir, a sirtuin inhibitor, nicotinamide, AIII, coumarin, sirtinol, alpha-NAD, carbamido-NAD, trichostatin A, suramin sodium, apicidin, BML-210, BML-266, depudecin, HC Toxin, ITSA1, nullscript, phenylbutyrate, sodium, scriptaid, splitomicin, suberoyl bis-hydroxamic acid, a sirtuin activators, resveratrol, isonicotinamide, butein, luteolin, plant extracts, hemp, nicotine, hemp derived compounds, terpenes, and any combination thereof.

In another aspect of the invention, the trans-epithelial membrane delivery system also includes transpiration barrier, wherein the transpiration barrier can be a chemical barrier or a physical barrier.

The present invention relates to methods for trans-epithelial membrane delivery of a formulation having an active ingredient to a mammal, wherein the mammal has a body surface that includes a stratum corneum, an epidermis, a basement membrane, and a dermis, in the case of skin, and saliva/mucus layer, stratified squamous epithelial layer, a basement member and lamina propria and smooth muscle, in the case of mucosal tissue. The steps of the method include applying the formulation, described herein, to the body surface. The agents of the formulation can be in a single step, in separate steps or the agents can be applied in any combination thereof to allow for delivery of the active ingredient. Accordingly, the method of the present invention can include, in one embodiment, the steps of administering at least one penetration agent to the body surface; administering at least one basement membrane disruptor to the body surface, wherein the basement membrane disruptor reversibly denatures or cleaves molecules in the basement membrane; administering at least one vaso-modulator; and administering at least one active ingredient, wherein the formulation allows for penetration of the active ingredient to the smooth muscle. Each of these agents are described herein. In one embodiment, the penetration agent, basement membrane, vaso-modulator, and active ingredient are applied sequentially, and in another method, they are applied in combination. The method can optionally further include applying an occlusive barrier to the body surface. The present invention further includes systems or kit for trans-epithelial membrane delivery of an active ingredient to a mammal. The kit or system encompasses the agents described herein and include at least one penetration agent, at least one basement membrane disruptor that reversibly denatures or cleaves molecules of the basement membrane; at least one vaso-modulator; and at least one active ingredient. The kit or system creates a formulation that allows for penetration of the active ingredient to the smooth muscle. In the case of a kit, the present invention also includes a set of written instructions for use, by or on said mammal.

Advantageously, the trans-epithelial membrane delivery formulation of the present invention results in an expanded range of active ingredients that can be delivered through the epithelial membrane. For example, by using the formulation of the present invention, more complex, higher molecular weight, and lower log-p active agents can be effectively delivered through the epithelium. The inventive formulation addresses a difficult-to-penetrate epithelial layer, the basement membrane, and allows for the passage of the active pharmaceutical agents into the smooth muscle and subsequent delivery into localized tissue or the blood stream. This delivery avoids side effects of orally delivered medications.

BRIEF DESCRIPTION OF THE DRAWINGS

FIG. 1 is a flow diagram showing the steps of method 100 of the trans-epithelial delivery system of the present invention.

DETAILED DESCRIPTION OF THE INVENTION

Figure 2:
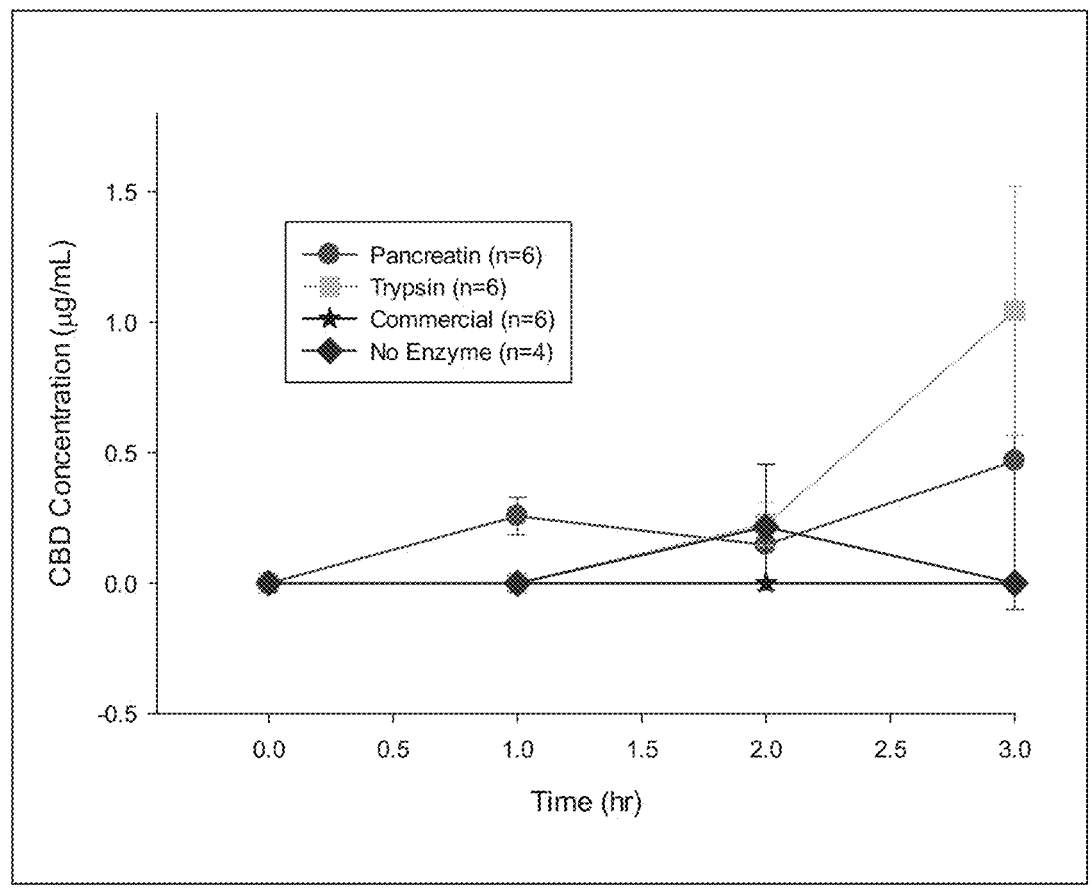
FIG. 2 is a line graph showing the CBD concentration in μg/mL over time (0-3 hours) for a formulation with no basement membrane disrupter, a commercial product, a formulation with trypsin as the basement membrane disrupter and a formulation with pancreatin as the basement membrane disrupter.

A description of preferred embodiments of the invention follows.

The skin, being the barrier organ of the body, consists of various structural layers. The layers of skin, starting from the outside, include the stratum corneum, epidermis, basement membrane and the dermis. The basement membrane is a very dense protein layer that separates the living tissue of the skin (dermis and smooth muscle) from the non-living skin layers (epidermis, stratum corneum). The basement membrane is one of the densest tissues in the human body. In the skin, it functions to not only prevent foreign particles from penetrating into living tissue (the dermis and smooth muscle), but it also functions to prevent fluids and living tissue constituents from moving out of the dermis and into the epidermis. In fact, in addition to providing a barrier and separation function, the basement membrane structurally anchors the epidermis to the dermis.

With respect to mucosal membranes, the layers of mucosal tissue, starting from the outside, include the stratified squamous epithelial layer, the basement membrane, the lamina propria, and smooth muscle. In the mouth, the cells of the outer stratified squamous epithelial layer are unkeratinized. This lipophilic layer covers the basement membrane which is a dense protein layer designed to prevent most permeation from foreign objects. In fact, the basement membrane functions to not only prevent foreign particles from penetrating into living tissue, but it also functions to prevent fluids and living tissue constituents from moving out to the stratified squamous epithelial layer. The basement membrane is formed from glycoproteins and is designed to also form the anchoring layer between the epithelial cells and the lamina propria (connective tissue) underlying the basement membrane. The lamina propria, the layer under the basement membrane, is the connective tissue layer which anchors the entire mucosa to the smooth muscle tissue underneath. Taken together, the three structures of the mucosa (epithelial cells, basement membrane and lamina propria), constitute an exceptionally difficult structure for foreign objects, like active drugs, to penetrate.

Another barrier of the mucosal tissue that the formulation of the present invention overcomes relates to mucosal secretions from mucosal tissue, which in the case of the mouth, is saliva. Saliva is approximately 99% water but also contains other components like electrolytes, mucus, epithelial cells, enzymes and antimicrobial agents. Specifically, mucin, the principal component in mucus, is a high molecular weight glycosylated protein which is secreted by the epithelial tissue solely as a penetration barrier. While saliva functions as a wetting agent and the commencement of the digestive process, it also effectively acts as a barrier to mucosal tissue penetration. Saliva solubilizes hydrophilic compounds, neutralizes acids and initiates the swallowing process. These functions work to thwart mucosal penetration and limit the potential impact of an active ingredient.

The inventive formulation allows for efficient transmucosal penetration and addresses the lack of access to the circulatory system. The epithelial layers contain no blood vessels. Neither does the basement membrane or the lamina propria. Although it is not vascularized, the lamina propria does contain a rich amount of plasma which feeds the epithelial cells by way of diffusion through the basement membrane. This passive indirect plasma flow effectively isolates any mucosal penetrant from any meaningful access to the circulatory system further thwarting an efficient transmucosal drug delivery system.

Both the skin and the mucosal membrane have outer layers (e.g., stratum corneum, epidermis of the skin, and mucus layer and stratified squamous epithelial layer of mucosal tissue), a basement membrane and smooth muscle. The present invention creates a formulation which can be placed onto an epithelial membrane that will do the following: 1. in the case of mucosal tissue, decrease the viscosity of and further solubilize into the mucosal secretion (saliva in the mouth); 2. Penetrate through the various outer epithelial layers and the basement membrane; and, 3. efficiently allow the active drug to access the circulatory system located within the smooth muscle tissue below the lamina propria (mucosal tissue) or dermis (skin).

Each layer is unique and designed to either limit the rate of penetration of a foreign matter or completely block its penetration. The present invention utilizes the concept that layers of the epithelial membrane, including the difficult-to-penetrate basement membrane, can be penetrated with certain chemical components. In particular, the present invention provides a novel trans-epithelial membrane delivery system that has a (e.g., one or more) basement membrane disruptor that allows for passage of the active ingredient through the basement membrane. In addition to the basement membrane disruptor, the trans-epithelial membrane delivery system of the present invention further includes a (e.g., one or more) penetration agent that allows for penetration of the outer layers and a delivery package that encompasses a (e.g., one or more) vaso-modulator and an (e.g., one or more) active ingredient.

The basement membrane consists of two major protein layers. The first protein layer is called the basil lamina. The basil lamina is a dense structural protein layer with a thickness of approximately 20 nm-100 nm consisting of Type IV collagen. This layer has two component layers: lumina lucida and lumina densa. The second layer in the basement membrane consists of reticular connective tissue which is made up of collagen and connects to the basil lamina. Left unaltered, the basement membrane layers synergistically work to either prevent active pharmaceutical movement into the smooth muscle or reduce the rate of flux to a level of sub-therapeutic drug flow. If the active pharmaceutical agent and the vasodilator are not able to move into the smooth muscle, the vasodilator will not be able to dilate the capillaries enhancing blood flow and allowing the active pharmaceutical agent to be picked up by the blood. This then allows it to move into deep local tissue or the blood stream for therapeutic benefit. Thus, using a basement membrane disruptor in the inventive delivery system allows for efficient permeation by the active drug compound through the basement membrane into the smooth muscle and from there into local tissue or the blood stream for therapeutic purposes.

In accordance with illustrative embodiments of the present invention, the inventive formulation relates to a trans-epithelial membrane drug delivery formulation that has at least three components. These component parts consist of: one or more penetration agents, one or more basement membrane disruptors and a delivery package with one or more active agents. In an embodiment, the formulation of the present invention when used e.g., for mucosal membranes has two penetrating agents. A first penetration agent is a digestive enzyme or proteolytic agent and the second penetration agent is a solvent, a lipophilic agent, a hydrophilic agent, or a combination thereof. Both of these penetration agents more fully described in more detail herein. A pH regulating agent, as further described herein, can be used in the formulation. In an embodiment, the pH regulating agent keeps the formulation at a pH between about 5.0 and 6.5 (e.g., 5.0, 5.1, 5.2, 5.3, 5.4, 5.5, 5.6, 5.7, 5.8, 5.9, 6.0, 6.1, 6.2, 6.3, 6.4, 6.5). In an embodiment, the pH regulating agent is designed to control the pH so that it is in a range between about 5 and about 6.5 (slightly acidic) which will provide for optimal penetration into the epithelial cell layers without generating excess saliva. Examples of pH regulating agents include citric acid, hydrochloric acid, potassium hydroxide, sodium hydroxide, sodium carbonate, sodium bicarbonate, and the like.

Each component can act or work by itself, or in combination with other agents/chemicals. In certain embodiments, some components can serve multiple roles. The penetration agents function by allowing the delivery package and basement membrane disruptors to pass through the outer layers of the skin or mucosal tissue and reach the basement membrane. The basement membrane disruptors function by temporarily or reversibly denaturing or cleaving molecules of the basement membrane. In an embodiment, the disrupter allows for basement membrane to denature/cleave and renature. During this action the basement membrane becomes permeable. This permeability then allows the delivery package to move to the smooth muscle. The delivery package, which encompasses the active pharmaceutical agents and optionally other agents, is now, if desired, positioned to move out of the smooth muscle and into either the blood stream or their intended therapeutic tissue.

In a particular embodiment, the present invention provides a novel trans-epithelial membrane delivery system that has one or more components described herein in a carrier vehicle, at a pH of between about 5 and about 6.5 to be delivered into the blood stream or deep tissue. The entire solute may contain excipients to provide stability and pH control.

FIG. 1 is a flow diagram, which outlines steps of method 100 for allowing an active agent to penetrate the epithelial membrane, thereby entering the smooth muscle, to deliver the active agent to localized tissue or the systemic circulation. The trans-epithelial membrane delivery formulation includes one or more penetration agents, one or more basement membrane disruptors and a delivery package which encompasses one or more active ingredients in combination with one or more vaso-modulator (e.g., a vasodilator or vasoconstrictor) (step 102). The formulation is applied to or within the epithelial membrane in step 104, and once applied, steps 106, 108 and 110 occur. Such application can be done with or without an applicator device (e.g., aerosol containers, spray containers, dissolving films, pastes, swab applicators and dropper applicators). Once the formulation is applied to the epithelial membrane, the penetration agent allows for passage of the basement membrane disruptor and the delivery package through the outer layers (e.g., the stratum corneum and the epidermis of the skin or the mucus and stratified squamous epithelial layer of the mucosal membrane) to the basement membrane in step 106. In step 108, the basement membrane disruptors induce reversible denaturing or cleaving of molecules and make the basement membrane permeable to allow for passage of the delivery package through the basement membrane to the smooth muscle. In an embodiment, the cellular spacing is increased to allow passage of the delivery package. Once past the basement membrane, the vaso-modulator, in step 110, causes a fluid dynamic event to deliver the active ingredient to the local tissue or systemically. In the case of mucosal tissue, a vasodilator used at Step 110 enhances plasma flow from the smooth muscle tissue and the enhanced flow picks up the active ingredient and moves it at increasing rates through these layers into local tissue or system circulation. Optionally, the formulation can include excipients, penetration enhancers, lipids, or other substances. The formulation can also be a patch or a component of a patch or similar drug delivery device.

Penetration Agents

Penetration agents refers to one or more agents that function to penetrate through both the outer layers of the skin (e.g., the stratum corneum layer and the epidermal layer of or mucosal membrane (e.g., mucus/saliva and stratified squamous epithelial layer) to the basement membrane. In the case of a transmucosal formulation, a first and second penetration agent can be used. In such an embodiment, a first penetration agent is used to penetrate the mucus/saliva layer. The first penetration agent can be a mucolytic agent. Mucolytic agents refer to a class of compounds that decrease the viscosity of mucus. Mucus is a secretion of epithelial tissue that consists of glycosylated proteins. These glycosylated proteins can pose a significant barrier to penetration into the epithelial tissue. Mucolytic agents for the inventive formation are those that thin or substantially diminish the viscosity of the mucus, thereby allowing the remaining components of the inventive formula to have enhanced contact directly with the epithelial tissue. Mucolytic compounds include by example but are not limited to acetylcysteine, N-acetylcysteine, L-cysteine, ambroxol, bromhexine, carbocisteine, erdosteine, mecysteine, dornase alfa, Althea extract, Marshmallow root, Bromelain, Thyme, Salt Water, Eucalyptol, Rosemary extract, Cineole, Peppermint, Frankincense, Oregano, Bergamot, Nutmeg, Cypress, Camphene, Geranium, *Pelargonium sidoides*, Cinnamon, Lemon, Citrus, D-limonene (citrus oils) or L-Limonenes (mint oils), Lavender, Lemon grass, Chamomile, and Basil.

In an embodiment, the first penetration agent (e.g., a mucolytic agent) can be included in the formulation in sufficient concentration (and therefore at sufficient activity) to thin or diminish the viscosity of the mucus. In an embodiment, a pharmaceutical transmucosal formulation includes a concentration of mucolytic agents/first penetration agent from about 0.01% w/w to about 10% w/w (e.g., 0.01, 0.05, 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.5, 4.0, 4.5, 5.0, 5.5, 6.0, 6.5, 7.0, 7.5, 8.0, 8.5, 9.0, 9.5, 10.0% w/w) of the formula. Such agents are commercially available from Millipore Sigma (St. Louis Missouri USA) or Fisher Scientific (Waltham Massachusetts USA). Mucolytic agents/first penetration agent now known, or developed in the future, can be used in the formulations of the inventive transmucosal delivery system so long as they thin or diminish the viscosity of the mucus to allow the rest of the formulation to contact the epithelial layer.

In an embodiment, the inventive formulation can include the first penetration agent, a second penetration agent, or both.

The second penetration agent includes one or more of the following: a solvent, a lipophilic agent, a hydrophilic agent, or a combination thereof. In an embodiment, the solvent used in the inventive trans-epithelial membrane delivery system can be one or more nonpolar solvents, one or more polar aprotic solvents (including dipolar aprotic solvents), one or more polar protic solvents, one or more limonenes, or combination thereof.

The penetration agent used in the present invention can be any combination of a solvent, a lipophilic agent, and/or a hydrophilic agent. A solvent can be used as the penetration agent alone or in combination with a lipophilic agent and/or a hydrophilic agent. In the case in which a solvent is not used, a combination of a lipophilic agent and/or a hydrophilic agent can be used to penetrate the stratum corneum layer and the epidermal layer of the skin or the mucus and stratified squamous epithelial layer of the mucosal layer. The penetration agents allow the basement membrane disruptor and delivery package to pass through these layers and arrive at the basement membrane.

Polar solvents are those that have large dipole moments (aka "partial charges") and generally contain bonds between atoms with very different electronegativities, such as oxygen and hydrogen. Polarity can be measured using the dielectric constant or from directly measuring the dipole moment.

Non-polar solvents generally have bonds between atoms with similar electronegativities, such as carbon and hydrogen. Examples of non-polar solvents encompass carbon tetrachloride (CCl4), benzene (C6H6), diethyl ether (CH3CH2OCH2CH3), hexane (CH3(CH2)4CH3), and methylene chloride (CH2Cl2). An example of a non-polar, protic solvent further includes toluene.

Furthermore, protic solvents are those that contain a hydrogen atom linked to an oxygen (hydroxyl group) or to a nitrogen (amine group). Protic solvents are able to donate protons (H+). Conversely, aprotic solvents are those that do not donate hydrogen and cannot hydrogen bond with themselves but may accept hydrogen. Polar protic agents have high dielectric constants and high polarity. Examples of polar protic solvents: water (H—OH), methanol, isopropanol, acetic acid (CH3CO—OH) methanol (CH3-OH), ethanol (CH3CH2-OH), n-propanol (CH3CH2CH2-OH), n-butanol (CH3CH2CH2CH2-OH). Polar aprotic solvents exhibit intermediate dielectric constants, they are polar and are highly miscible in water. Examples of polar aprotic solvents are propylene carbonate. Examples of dipolar aprotic solvents include: acetone ((CH3)2C═O), ethyl acetate (CH3CO2CH2CH3), dimethyl sulfoxide ((CH3)2SO) ("DMSO"), acetonitrile (CH3CN), and dimethylformamide ((CH3)2NC(O)H). In an embodiment, polar protic and/or polar aprotic solvents are preferred.

Limonenes used as a solvent in the present invention to penetrate the outer layers (e.g., stratum corneum layer and the epidermis) include D-limonene (citrus oils) or L-Limonenes (mint oils), and optionally together with a liquid hydrocarbon.

Additional examples of some penetration agents include individual fatty acids, fatty acid esters, polyols, amides, various anionic, cationic and nonionic surfactants such as but not limited to sodium laurate and sodium lauryl sulfate, phospholipids, cholesterol and cholesterol derivatives, m-pyrrole, dimethyl acetamide, limonene, sphingo lipids, ceramides, terpenes, alkanones, menthol, various organic acids, such as but not limited to salicylic acid, citric and succininc acid, prostaglandins, decyl-methyl sulfoxide, sulfoxide alcohols, plant extract oils. Suitable fatty acids include without limitation: linoleic acids, linolenic acids, oleic acids, stearic acids, and myristic acids. Phospholipids include without limitation: phosphatidylcholine, phosphatidylethanolamine, and phosphatidylserine. Plant extract oils include, but are not limited to, oils of peanut, grape seed, hemp, borage, tea tree, winter green, lemon, olive, sunflower, soy-bean, eucalyptus, monoi and macadamia. The plant extract oil can be mixed with an alcohol such as ethyl alcohol, isopropyl alcohol, and methyl alcohol. Penetration agents can also include vitamins for example like vitamin E, C or D.

Some penetration agents are commercially available from Fisher Scientific (Pittsburgh Pennsylvania, USA), Spectrum Chemical MFG Corp (New Brunswick, New Jersey, USA), or BASF (Florham Park New Jersey, USA). Penetration agents now known, or developed in the future, can be used in the compositions and methods of the inventive trans-epithelial membrane delivery system so long as the penetration agents allow for penetration of the basement membrane disruptor and delivery package through the outer layers of the epithelial membrane (e.g., stratum corneum layer and/or epidermal layer of the skin or stratified squamous epithelial layer of the mucosa).

In an embodiment, the penetration agent can be included in the formulation in sufficient concentration and in effective amounts to allow for penetration through the outer layers of the epithelium to the basement membrane. In an embodiment, a pharmaceutical trans-epithelial membrane formulation includes a concentration of penetration agents ranging from about 0.01% w/w to about 90% w/w (e.g., 0.01, 0.5, 1, 1.5, 2.0, 5.0, 10.0, 15.0, 20.0, 25.0, 30.0, 35.0, 40.0, 45.0, 50.0, 55.0, 60.0%, 65.0, 70.0, 75.0, 80.0, 85.0, 90.0% w/w). In an embodiment, the trans-epithelial membrane formulation of the present invention includes the first penetration agent an amount ranging from about 0.01% w/w to about 2.0%.

Basement Membrane Disruptors

The trans-epithelial membrane delivery system and methods of the present invention utilize one or more basement membrane disruptors. They are agents that cause the basement membrane to become permeable. A basement membrane disruptor can be used by itself or in combination with other basement membrane disruptors. By using these disruptors in the trans-epithelial membrane formulation and having the penetration agents move them to the basement membrane, the proteins or molecules in the basement membrane will be reversibly denatured and/or cleaved. This denaturing process disrupts the quaternary, tertiary and/or secondary structures of the protein. Disrupting these structures will reversibly and temporarily alter the shape and confirmation of the protein allowing for permeability through the basement membrane and therefore allow for penetration of the delivery package of the trans-epithelial membrane delivery system.

Examples of basement membrane disruptor agents include one or more chaotropic agents or one or more other agents that allow for denaturing or permeability of the basement membrane proteins, or a combination thereof. Chaotropic agents are agents that disrupt the hydrogen bonding network between water molecules. Examples of a basement membrane disruptors include guanidine hydrochloride, a guanidine salt, guanidine analogs, guanidine conjugates or any combination thereof. An analog, as used herein, is a compound that has similar structural, physical, chemical, biochemical, functional, or pharmacological properties to that of guanidine, and is able to reversibly denature the basement membrane.

Additionally, examples of basement membrane disrupters include one or more proteolytic agents, proteases, or enzymes. A protease (also called a peptidase or proteinase) is an enzyme that catalyzes or increases the rate of proteolysis, the breakdown of proteins into smaller polypeptides or single amino acids. As used herein, basement membrane disrupters are those that cleave or fragment long chain proteins to create cellular spacing. A basement membrane disrupter can be used by itself in the inventive formulation, or in combination with others. Basement membrane disrupters in the inventive formulation cleave the proteins or molecules in these layers. This protein cleavage causes cellular spacing to thereby allow the vasodilator and active ingredient to move through to the smooth muscle.

Basement membrane disrupters include proteolytic enzymes or proteases and refer to any enzymes that can cleave or fragmentize long chain proteins or molecules to create cellular spacing. There are various classes of proteases that can be included in the formulation of the present invention. Such proteases include Serine Proteases (e.g., Subtilisin, Prolyl oligopeptidase, D-Ala-D-Ala peptidase C, Cytomegalovirus assemblin, Lon-A peptidase, Clp protease, Phage KIF endosialidase CIMCD self-cleaving protein, Nucleoporin 145, Lactoferrin, Murein tetrapeptidase LD-carboxypeptidase, Rhomboid-1, Chymotrypsin A, α-trypsin, and β-trypsin, Penicillin G acylase precursor, Dipeptidase E, DmpA aminopeptidase), Cysteine Proteases (e.g., Papain, bromelain, cathepsin K, calpain, Caspase-1, Adenain, Pyroglutamyl-peptidase I, Sortase A, Hepatitis C virus peptidase 2, Sindbis virus-type nsP2 peptidase, Dipeptidyl-peptidase VI, DeSI-1 peptidase, TEV protease, Amidophosphoribosyltransferase precursor, Gamma-glutamyl hydrolase, Hedgehog protein, DmpA aminopeptidase), Threonine Proteases (e.g., archaean proteasome, beta component, ornithine acetyltransferase), Aspartic Proteases (e.g., BACE1, BACE2, Cathepsin D, Cathepsin E, Chymosin, Napsin-A, Nepenthesin, Pepsin, Presenilin, Renin), Glutamic Proteases (e.g., scytalidoglutamic peptidase (eqolisin) and aspergilloglutamic peptidase), Metalloproteases (e.g., Exopeptidases, metalloexopeptidases), Asparagine Peptide Lyases, and Glucanases. Examples of specific proteolytic enzymes include but are not limited to Amyl glucosidase, Alpha-Amylase, Amylase, Alpha-Glucanase, Beta-Glucanase, Glactomannase, Hemicellulase, Acid Protease, Alkaline Protease, Cellulase I, Cellulase II, Lipase, Lactase, Serratio Peptidase, Exo-Peptidase, Endo-Peptidase, Betaine, Maltase, Ox Bile Extract, Phytase, Pancreatin, Pepsin, Protease I-IV, Pullulanase, Sucrase, Protease Invertase, Pectinase, Papain, Papaya, Apple Pectin, Ginger, Tumeric, Bromelain, Pineapple, and Peppermint. In an embodiment, the basement membrane disruptors include a serine protease, a cysteine protease, a threonine protease, an aspartic protease, a glutamic protease, a lipase, a lactase, an ox bile extract, a phytase, a pancreatin, a pepsin, Chymotrypsin A, α-trypsin, and β-trypsin, papain, papaya, bromelain, and pineapple, In an embodiment, the basement membrane disruptor can be included in the formulation in sufficient concentration (and therefore at sufficient activity) to create a condition of reversible denaturing and/or cleaving of the proteins in the basement membrane. In an embodiment, a pharmaceutical trans-epithelial membrane formulation includes a concentration of basement permeation disruptors from about 0.2% w/w to about 10% w/w (e.g., 0.2, 0.3, 0.0.4, 0.5, 0.0.6, 0.7, 0.8, 0.9, 1, 1.2, 1.4, 1.6, 1.8, 2.0, 2.2, 2.4, 2.6, 2.8, 3.0, 3.5, 4.0, 4.5, 5.0, 5.5, 6.0, 6.5, 7.0, 7.5, 8.0, 8.5, 9.0, 9.5% w/w) of the formula. Concentrations at this level will cause only a temporary or reversible denaturing of the basement membrane proteins and not interfere with the primary structures. Once the disruptor has passed through basement membrane, they will begin to regain their original structure (renature). Such basement permeation disruptors are commercially available from Sigma Aldrich (St. Louis Missouri USA) or Thermo Fischer Scientific (Waltham Massachusetts USA). Basement membrane disruptors now known, or developed in the future, can be used in the formulations of the inventive trans-epithelial membrane delivery system so long as the disruptor causes permeability of the basement membrane or reversibly denatures or cleaves molecules (e.g., proteins) of the basement membrane.

Delivery Package

The delivery package includes the active pharmaceutical agents that are targeted to reach the living epithelial membrane layer (dermis, lamina propria, smooth muscle). The delivery package includes at least two types of compounds: the therapeutic drug or drugs having an "active agent" or "active ingredient" and a vaso-modulating agent.

Therapeutic Drugs, Active Drugs or Active Chemical Ingredient Components

A "therapeutic drug," "active agent" or an "active ingredient" are interchangeable and refers to any component of a formulation that provides pharmacological activity or other direct effect in the diagnosis, cure, mitigation, treatment, amelioration, or prevention of disease, condition or disorder. Further, an active ingredient or active chemical ingredient can include any plant extract, essential oil, isolate, distillate or biologic. Examples of active ingredients that are useful in the topically applied pharmaceutical formulations and methods of the instant invention include antifungal agents; anti-inflammatory agents, such as non-steroidal anti-inflammatory drugs (NSAIDS) and steroidal anti-inflammatory drugs; antibiotics; antiviral agents; anti-neoplastic agents; astringents; anesthetics; systemic drugs; steroid hormones, such as estradiol and testosterone; cosmetic agents, such as skin moisturizers, protectants, and emollients; nutrients, such as vitamins; and ceramides, and other known to those skilled in the art (e.g., those ingredients listed by the U.S. Food and Drug Agency in "Approved Drug Products with Therapeutic Equivalence Evaluations (Orange Book)", available at: http://www.fda.gov/Drugs/InformationOnDrugs/ucm129662.htm that are judged suitable by those skilled in the art), the entire teaches are hereby incorporated by reference. https://www.fda.gov/drugs/drug-approvals-and-databases/approved-drug-products-therapeutic-equivalence-evaluations-orange-book that are judged suitable by those skilled in the art). In an embodiment, the active ingredient is capable of inducing a desired physiological effect on a targeted mucosa or other tissue other than solely a vasodilatory or vasoconstrictory effect.

Specific examples of active ingredients include acetaminophen, acetohydoxamic acid, acetophenazine, acyclovir, albuterol, allopurinol, amiloride, amoxicillin, amphetamine, ampicillin, antisense polymers, atenolol, baclofen, beclomethasone, benfotiamine, betamethasone, budesonide, bumetanide, butorphanol, carbamazepine, carphenazine, celacoxhib, cefuroxime, cephradine, chloramphenicol, chlorothiazide, chlorzoxazone, cinoxacin, clorazepate, cloxacillin, cyclacillin, dapsone, dicloxacillin, diethylstilbestrol, dopamine, doxorubicin, erythropoietin, estradiol, fenoprofen, gabapentin, human growth hormone, hydralazine, hydrochlorothiazide, ibuprofen, indomethacin, insulin, isoproterenol, ketoprofen, levodopa, levothyroxine, lidocaine hydrochloride, meclofenamate, melphalan, metformin methyl salicylate, metronidazole, minoxidil, morphine, nadolol, nalidixic acid, naproxen, nomifensine, norfloxacin, oxaprozin, oxycontin, paramethasone, peptide fragments, perphenazine, phenylpropanolamine, pregabalin, probenecid, quinethazone, ritodrine, scopolamine, serotonin, sildenafil, tadalafil, terbutaline, terfenadine, tocainide, terbinafine, triamterene, riamterine, trimethoprim, valacyclovir and any derivatives of these and combinations of the foregoing. The active ingredient can also be a sirtuin inhibitors such as nicotinamide, AIII, coumarin, sirtinol, alpha-NAD, carbamido-NAD, trichostatin A, suramin sodium, apicidin, BML-210, BML-266, depudecin, HC Toxin, ITSA1, nullscript, phenylbutyrate, sodium, scriptaid, splitomicin, or suberoyl bis-hydroxamic acid. Further, the active ingredient can be sirtuin activators such as resveratrol, isonicotinamide, butein, or luteolin. In addition, active ingredients can also be compounds extracted from plants including hemp and cannabis in all of their forms including compounds like CBD, THC, terpenes, essential oils, extracts, isolates, etc. Therapeutic drug or active ingredients now known, or developed in the future, can be used in the compositions and methods of the inventive trans-epithelial membrane delivery system so long as the therapeutic drug or active ingredients can be delivered to the vasculature of the smooth muscle.

In some embodiments of the invention, the active ingredient comprises a biological agent. Examples of biological agents include peptides, small proteins and protein fragments; antibody fragments; small nucleic acids and nucleic acid fragments such as aptamers and siRNA; or combinations of these.

In an embodiment, the active ingredient can be included in the formulation in sufficient concentration and in effective amounts to confer the desired effect of the active ingredient. The actual effective amounts of the active agent/ingredient or drug can vary according to the specific composition being utilized, the age, weight and condition of the patient. Dosages for a particular individual patient can be determined by one of ordinary skill in the art using conventional considerations, (e.g. by means of an appropriate, conventional pharmacological protocol). In an aspect, dosing will also depend on the therapeutic effect to be achieved for the disease state. In general, the amount of active ingredient present in the inventive formulation ranges from about 0.001% w/w to about 30% w/w (e.g., 0.001, 0.005, 0.01, 0.05, 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30% w/w).

A Vaso-Modulating Agent

A "vaso-modulating agent" or "vasoactive agent" refer to either a vasodilator or a vasoconstrictor component of a formulation, and includes pro-drugs of such components. In other words, "vaso-modulating agent" or "vasoactive agent" are agents that create intra-epithelium fluid dynamic events.

The vaso-modulating agent is the active chemical agent designed to create a fluid dynamic event in the smooth muscle in order to move the therapeutic drug from the epithelial membrane into either the blood stream, lymphatic system or deep into local tissue so that the drug can impart therapeutic benefit. In an embodiment in which the target is the epithelial membrane itself, then a vaso-modulating agent may not be needed and is optional, or a vasoconstrictor can be used to keep the active agent local. In an embodiment in which therapy is attempting to increase blood flow into local tissue, then the vaso-modulating agent acts also as the therapeutic drug. In another embodiment, a vasodilating agent can be included in the formulation in sufficient concentration and in effective amounts to create a fluid dynamic event in the smooth muscle in order to move the therapeutic drug from the epithelial membrane into either the blood stream, lymphatic system or deep into local tissue. In an embodiment, a pharmaceutical trans-epithelial membrane formulation includes a concentration of vaso-modulating agent from about 0.001% w/w to about 15% w/w (e.g., 0.001, 0.005, 0.01, 0.05, 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, or 15% w/w) of the formula.

The vascular modifying agent can be a vasodilator. The vasodilator can be in an amount that is effective to cause dilation of capillaries in the smooth muscle, increased blood and fluid flow through the capillaries in the smooth muscle, and/or increased permeation of fluid through the walls of blood vessels of the patient. The species of vasodilator can be chosen depending on the speed with which the active drug should move from the smooth muscle and therefore affect the tissue being targeted. Aggressive vasodilators like tolazoline, sodium nitroprusside and papaverine can be used to quickly move the active drug into the bloodstream. Mild vasodilators like arginine can be used to slowly release the drug into the blood stream so that it can be predominately taken up by the localized tissue or provide release over an extended period of time.

The vasodilator (or mixture of vasodilators) in the formulation can be chosen from the classes of endothelium-dependent vasodilators, endothelium-independent vasodilators and prostaglandin-based vasodilators to elicit the production of endogenous prostaglandins. Prodrugs of any of the foregoing vasodilators can also be used. In an embodiment, inclusion of the vasodilator in the formulation will relax or dilate the arteries and arterioles and therefore increase the volume of flow into the capillary network. This increased volume of blood will subsequently result in an increased trans-capillary flux of water from the vessel into the surrounding tissue.

Vasodilators include, for example, amrinone, arginine, bamethan sulphate, bencyclane fumarate, benfurodil hemisuccinate, benzyl nicotinate, buflomedil hydrochloride, buphenine hydrochloride, butalamine hydrochloride, cetiedil citrate, ciclonicate, cinepazide maleate, cyclandelate, di isopropylammonium dichloroacetate, ethyl nicotinate, hepronicate, hexyl nicotinate, ifenprodil tartrate, inositol nicotinate, isoxsuprine hydrochloride, kallidinogenase, methyl nicotinate, naftidrofuryl oxalate, nicametate citrate, niceritrol, nicoboxil, nicofuranose, nicotinyl alcohol, nicotinyl alcohol tartrate, nitric oxide, nonivamide, oxpentifylline, papaverine, papaveroline, pentifylline, peroxynitrite, pinacidil, pipratecol, propentofyltine, raubasine, suloctidil, teasuprine, thymoxamine hydrochloride, tocopherol nicotinate, tolazoline, papaverine, xanthinol nicotinate, diazoxide, hydralazine, minoxidil, and sodium nitroprusside. Centrally acting agents include clonidine, quanaberz, and methyl dopa. Alpha adrenoceptor blocking agents include indoramin, phenoxybenzamine, phentolamine, and prazosin. PDE-5 inhibitors including sildenafil, tadalafil. Adrenergic neuron blocking agents include bedmidine, debrisoquine, and guanethidine. ACE inhibitors include benazepril, captopril, cilazapril, enalapril, fosinopril, lisinopril, perindopril, quinapril, and ramipril. Ganglion blocking agents include pentolinium and trimetaphan. Calcium channel blockers include amlodipine, diltiazem, felodipine, isradipine, nicardipine, nifedipine, nimodipine, and verapamil. Prostaglandins including: prostacyclin, thrombuxane A2, leukotrienes, PGA, PGA1, PGA2, PGE1, PGE2, PGD, PGG, and PGH. Angiotensin II analogs include saralasin. Other suitable vasodilators include nitroglycerin, labetalol, thrazide, isosorbide dinitrate, pentaerythritol tetranitrate, digitalis, hydralazine, diazoxide, and sodium nitroprusside, derivatives of these and combinations of the foregoing. Also, natural vasodilators can be used in the inventive formulation. Natural vasodilators include cinnamaldehyde, tea tree oil, eucalyptus, lemon, coriander, peppermint, helichrysum, cistus, cypress, lentisque, juniper berry, niaouli, ginger, rosemary, basil, sage, geranium and cumin. Also included are some arginine derivatives, acetylcholine, sodium nitroprusside, methyl nicotinate, hexyl nicotinate, arachidonic acid, prostaglandin D2, prostaglandin I2, tolazoline, and papaverine. Arginine is a known substrate for nitric oxide synthase and it is known that nitric oxide can exert a vasodilatory effect.

Vasodilators for use with the present invention are commercially available, for example, from Sigma Aldrich (St. Louis Missouri USA), BASF (Florham Park New Jersey, USA), or Hawaii-Pharm (Honolulu, Hawaii (USA). Vasodilators now known, or developed in the future, can be used in the compositions and methods of the inventive trans-epithelial membrane delivery system so long as the vasodilators creates a fluid dynamic event in the epithelium to move the therapeutic drug into either the blood stream, lymphatic system or deep into local tissue.

In an embodiment, the vascular modifying agents can be vasoconstrictors in order to keep the active ingredient/active drug in the epithelial membrane (e.g., at the dermis, smooth muscle) to treat skin disorders or the like. A vasoconstrictor that can be used in the present invention includes an agent that narrows blood vessels in the smooth muscle. A vasoconstrictor can be used in the instance when local tissue is targeted. The vasoconstrictor allows the active ingredient to remain localized and reduces or eliminates release into systemic circulation. Examples of vasoconstrictors include adenosine triphosphate, amphetamine, antazoline, asymmetric dimethylarginine, cocaine, dopamine, endothelin, ephedrine, epinephrine, ergine, hydroxyamphetamine, isoproterenol, levonordefrin, metaraminol, methamphetamine, methoxamine, methylphenidate, neuropeptide Y, naphazoline, norepinephrine, oxymetazoline, phenylephrine, pseudoephedrine, tetrahydozoline, thromboxane, tramazoline, tyramine, derivatives of these and combinations of the foregoing. Such vasoconstrictors are commercially available, for example, from Spectrum Chemical MFG Corp (New Brunswick, New Jersey, USA), BASF (Florham Park New Jersey, USA), or Thermo Fischer Scientific (Waltham Massachusetts USA). Vasoconstrictors now known, or developed in the future, can be used in the compositions and methods of the inventive trans-epithelial membrane delivery system so long as the vasoconstrictors creates a fluid dynamic event in the epithelium involving a narrowing of the blood vessels to keep the active ingredient in the epithelium and prevent or reduce release of the active ingredient from the epithelial membrane.

The vasoactive agent can be chosen to exert effects rapidly (e.g., within 10 minutes or less), over a longer period of time (e.g., over the course of an hour or more). The vasoactive agent can also be chosen to give a delayed release (e.g., release begins after 10 minutes). Multiple vasoactive agents can be combined to result in both rapid and longer-term effects on the epithelial membrane.

The trans-epithelial membrane delivery system of the present invention can be a formulation having the agents described herein. A "formulation" is a preparation in which various chemical substances are combined with an active ingredient. As used herein, a formulation includes a composition of the invention in the form of an emulsion, ointment, cream, lotion, gel, spray, salve or the like, for topical application or delivery of the drug to a patient. In some embodiments, as appropriate, a formulation is used in conjunction with a delivery system (such as a patch or quick dissolve film) impregnated with or containing a composition suitable for topical application. The term "patient" or "individual" refers to any animal, including mammals such as a human, non-human primate, mouse, rat, guinea pig, rabbit, pig, horse or dog.

The trans-epithelial membrane delivery system is applied topically to an individual. "Topical" application shall mean direct application of a formulation to body surfaces such as the skin or mucous membranes, for example, oral mucosa (e.g., tongue, cheek, buccal pouch), vaginal mucosa, anal mucosa, tracheal mucosa, lung mucosa, throat mucosa, nasal mucosa, ocular mucosa, and ear mucosa. For purposes of applying a formula, topical application shall include application to the stratum corneum or stratified squamous epithelial layer, microinjection to the outer layers (such as can be achieved with microneedles), or use of devices such as films, aerosols, liquid, sprays, pastes, patches, sonophoresis, iontophoresis or other permeation-enhancing methods, and subsequent injection to structures.

In general, the application of the topical/trans-epithelial membrane formulation of the components, e.g., the components of the penetration agent, basement membrane disruptor and delivery package, can occur simultaneously or sequentially in time. Thus, the term "co-administration" is used herein to mean that the components of the trans-epithelial membrane delivery system will be administered at times to achieve delivery of the active ingredient. In an embodiment, the formulation is applied in order to penetrate layers of the epithelial membrane, starting from the outside layers and going inward. Accordingly, in an embodiment, the penetration agents are applied first, then the basement disruptors and subsequently or simultaneously the delivery package. In other embodiments, the methods of the present invention are not limited to the sequence in which the compounds are administered, so long as the delivery package penetrates through the outer layers of the epithelial membrane to the smooth muscle. A transpiration barrier can also be applied sequentially with respect to the other components one or more times.

In some embodiments, the functions of two or more penetration agents, basement membrane disruptors and/or vaso-modulators can be provided by a single compound. In other words, in an embodiment, a single compound can have more than one function, and act as a penetration agent, a basement membrane disruptor and/or a vaso-modulator.

In some embodiments the trans-epithelial membrane delivery formula may be used with a transpiration barrier or an occlusive barrier. A "transpiration barrier" shall mean a component such as a solid patch, a hydrophobic chemical component, or a self-assembling chemical component (including components that form gels) that is capable of preventing water loss from epithelial membrane tissue due to transpiration when applied to the skin of a patient. An "occlusive barrier" can be used to apply the formula to the epithelial membrane or other tissue (e.g., application device), to prevent against cross contamination of clothes or other individuals (e.g., barrier device), to allow for timed release or enhanced delivery (e.g., delivery device). In an embodiment, the occlusive barrier is in the form of a physical patch like material, a tegaderm like barrier material, or a transpirational barrier (silicone, vasoline etc).

In an embodiment, the method includes optionally applying a transpiration barrier. The transpiration barrier can be a water impermeable drug administration patch; for example, a sheet of water-resistant plastic with an adhesive layer or other attachment mechanism. The patch can be applied atop a formulation applied to the epithelial membrane. Alternately, the patch can be impregnated with the formulation and applied to the epithelial membrane to contact the vaso-modulator agent, active ingredient, the basement membrane or the penetration agent with the epithelial membrane while forming the transpiration barrier. A water-impermeable wrap, glove, sock, mitten, or the like can also serve to create a physical barrier. Alternately, or in addition, the transpiration barrier can include a molecular (i.e., chemical) barrier; i.e., one that contains a plurality of molecules or particles that are at least initially unbonded and which dry on or embed in the epithelial membrane to produce a moisture-resistant barrier. For example, the molecular barrier can include silicone, titanium oxide, polyvinyl alcohol and hydrogels. It should be noted that both a chemical barrier and a physical barrier can be used together or sequentially.

The formulation can optionally further include penetration enhancers, agents that improve or boost passage of the active ingredient to the smooth muscle. Examples of penetration enhancers include individual fatty acids, fatty acid esters, polyols, amides, various anionic, cationic and non-ionic surfactants such as but not limited to sodium laurate and sodium lauryl sulfate, phospholipids, cholesterol and cholesterol derivatives, m-pyrrole, dimethyl acetamide, limonene, sphingolipids, ceramides, terpenes, alkenones, menthol, and various organic acids, such as but not limited to salicylic acid, citric and succinic acid, prostaglandins, decyl methyl sulfoxide, urea, sulfoxide alcohols, and plant extract oils. Suitable fatty acids include without limitation linoleic acids, linolenic acids, oleic acids, stearic acids, and myristic acids. Phospholipids include without limitation phosphatidylcholine, phosphatidylethanolamine, and phosphatidylserine. Plant extract oils include oils of peanut, hemp, borage, olive, sunflower, soybean, monoi and macadamia. The plant extract oil can be mixed with an alcohol such as ethyl alcohol, isopropyl alcohol, and methyl alcohol.

The formulation can be applied to the epithelial membrane; i.e., topically (step 104). For example, the formulation can be a cream, lotion, ointment, gel, or other substance suitable for topical application to the epithelial membrane. Optionally, the epithelial membrane can be mechanically worked to enhance the penetration of the active ingredient past the epidermis (e.g., into or through the basement membrane). For example, mechanical work can be used in the form of massaging, or sonophoresis. Mechanical working processes also include processes of cutting, ulceration, wound formation or piercing. For example, piercing the epithelial membrane with microneedles (e.g., with a device having projections designed to pierce the stratum corneum or stratified squamous epithelial layer without the substantial triggering of deeper pain receptors) can aid in the drug delivery process. Microneedles are disclosed, for example, in U.S. Pat. No. 6,611,707, issued on Aug. 26, 2003 to Prausnitz, which is incorporated herein by reference in its entirety. Sonophoresis (e.g., via ultrasound) can also be used to exert mechanical work and enhance penetration. Electrical work can also be employed; e.g., iontophoresis. The above list is an illustrative and not exhaustive list of working processes that can be employed in connection with embodiments of the present invention. Optionally, the formulation can be delivered into the epithelial membrane. For example, the formulation can be injected into the epithelial membrane with microneedles.

The formulation can also include excipients or carriers such as Stearyl Alcohol, Polysorbate 20, Caprylic/Capric Glyceride, Petrolatum, Beeswax, Lecithin, Dimethicone, Alkylmethyl Siloxane, Stearic Acid, Palmitic Acid, Lanolin, Linoleic Acid, Isopropyl Myristate, Stearyl Octanoate and Cetyl Octanoate, and Polysorbate 80.

In addition, the present invention can be used with or without a device for the convenient application onto the mucosal tissue. Examples of various devices include, but are not limited to aerosol containers, spray containers, dissolving films, pastes swab applicators and dropper applicators.

Embodiments of the invention can be useful for medical conditions, diseases or disorders such as musculoskeletal diseases, vascular diseases, neurological diseases, viral, bacterial or parasitic diseases, blood disorders, skin diseases, autoimmune diseases, organ diseases, pain, and others. The number of diseases is numerous, but some examples include basal cell carcinomas, melanoma, cervical carcinomas, cervical condylomas, genital warts, herpetic lesions, diabetic neuropathy, chemotherapy-derived neuropathy, general neuropathy, benign prostatic hypertrophy, solid tumors, psoriasis, and eczema. In some embodiments, the active ingredient is a sirtuin inhibitor or sirtuin activator and the formulation is applied to the epithelial membrane of a patient to treat one of these medical conditions. Where accessible, the formulation can be applied to a region of the epithelial membrane or tissue associated with the medical condition.

In some embodiments of the invention, the formulation is cosmetically suitable in that it can be applied to the epithelial membrane without detrimentally affecting the appearance of the epithelial membrane.

In addition to application to the epithelial membrane, the formulation can be applied to any exterior regions of the body including skin, oral mucosa (e.g., tongue, cheek, buccal pouch), vaginal mucosa, anal (rectal) mucosa (as a suppository), throat mucosa, nasal mucosa, or ocular tissue, tracheal mucosa, lungs, fingernails, toenails, and any other tissue surfaces containing an epithelial membrane.

A formulation can be tested for its ability to increase circulation using laser Doppler velocimetry measurements. Such measurements are known in the art (see, e.g., Holloway G A Jr, Watkins D W., 1977, Laser Doppler measurement of cutaneous blood flow. J Invest Dermatol., September; 69(3):306-9). The test can be performed on participants after a 20-minute acclimatization period in a warm environment (room temperature 24° C.). For each subject, the blood flow response is measured with the non-invasive test before and after the application of the test formulation and at various intervals of time after the application until the blood flow has returned to a pre-application level. The measurement of epithelial membrane blood flow can be evaluated using a Laser Doppler Perfusion Imager (LDPI Lisca 2.0, Lisca development AB, Linkoping, Sweden). This apparatus employs a 1 mW Helium-Neon laser beam of 633 nm wavelength, which sequentially scans the tested area. Typically, the maximum number of measured spots is 4096 and the apparatus produces a color-coded image of the tissue perfusion distribution on a computer monitor. The data acquired from the instrument can be statistically analyzed with The Minitab statistical package (Minitab, State College, Pa.) for personal computers. For intra-group comparisons, the paired t-test can be used to compare changes between baseline and the maximal vasodilation. The test can be used for comparison between the two groups of patients. Changes in the microvascular blood flow can be expressed as the difference between the peak response and the baseline blood flow (e.g., in ml/min, laser-doppler velocimetry voltage readout, or other suitable units).

In some embodiments of the invention, application of the formulation can cause an increase in blood flow at or near the region of application. The increase can range from about 1% to greater than about 500%.

Animal models can be used to evaluate the effectiveness of a topically applied formulation in penetrating the epithelial membrane tissue for either intrad- or trans-epithelial membrane systemic distribution of the active ingredient. Animal models that are preferred include pigs, guinea pigs, rabbit and mini-pigs. An example of the procedure used for such a study using guinea pigs is as follows: Male Hartley guinea pigs (250-300 g) are shaved on the back, and an area of 4×4 cm depilated with Nair® depilatory cream. After approximately 24 hours, 0.5 g of test compound in a topical formulation is applied to the 4×4 cm area and covered with an occlusive wrap. At 1, 2, 4, 8 and 24 hours after application, groups of >5 animals are anesthetized with isoflurane, the application area is swabbed with alcohol, blood is removed by cardiac stick, and the epithelial membrane tissue of the application area is excised. One group of animals is anesthetized and blood and epithelial membrane tissue are removed as vehicle control. Blood samples are processed to serum and analyzed for the presence of an active ingredient via HPLC. The epithelial membrane below the area of compound application on each animal group is excised, weighed, homogenized in a mixture of acetonitrile and 0.1N HCl (50:50 v/v), centrifuged, and the extract analyzed for the presence of active ingredient via HPLC via HPLC. The amount of active ingredient in the blood and the amount of active ingredient in the epithelial membrane tissue may be compared to give information about the pharmacokinetics of the active ingredient. For delivery to local tissue, a higher amount in the epithelial membrane relative to the blood is more efficacious, whereas when the goal is systemic delivery of the active ingredient, a higher distribution in the blood is more efficacious.

The trans-epithelial membrane delivery system of the present invention is effective in delivering the active ingredient. In some embodiments, the inventive trans-epithelial membrane delivery system is as effective in delivering the active ingredient, as compared to traditional methods of administration such as oral administration. In the case of certain embodiments, the inventive trans-epithelial membrane delivery system delivers the active ingredient more effectively, as compared to its oral administration or other trans-epithelial membrane administrations (at least about 5, 10, 15, 20, 25, 30, 35, 40, 45, 50, 55, 60, 65, 70, 75, 80, 85, 90, 95, or 100% more effective).

In another embodiment, a kit or system is used for topical or trans-epithelial membrane delivery of an active ingredient to a patient. The kit includes one or more of the following: a penetration agent, a basement membrane disruptor and a delivery package comprising a vaso-modulator and active ingredient. The kit can also include a set of written instructions for use thereof according to one of the methods of topical or trans-epithelial membrane delivery described herein. The kit optionally includes an occlusive barrier.

In yet another embodiment, a kit is supplied to a compounder. The kit contains the components/agents described herein (e.g., a penetration agent, a basement membrane disruptor and a delivery package) and it allows the compound pharmacist to manufacture the formulation of the present invention.

In another embodiment, there is a method of manufacturing a medicament for trans-epithelial membrane administration. The method includes combining a penetration agent, a basement membrane disruptor and a delivery package comprising a vaso-modulator and active ingredient in sufficient amounts to cause permeation of the active ingredient to at least one affected region of a patient when applied to one of the epithelial membrane and other exterior region of the patient.

EXEMPLIFICATION

Example 1

Part A

| Component | % w/w |
| --- | --- |
| Water | 71.5 |
| Carbomer 940 (Thickener) | 1 |
| Guanidine HCl (Basement Membrane Disrupter/Chaotropic Agent) | 0.5 |
| Glycerin (Humectant) | 2 |
| Caffeine (Active Ingredient) | 1 |
| Urea (Humectant) | 5 |
| Arginine HCl (Vaso-modulator/Vasodilator) | 0.5 |

Part B

| Component | |
| --- | --- |
| Oleic Acid (Emulsifier/Penetration Enhancer/Agent) | 3 |
| Glyceryl Monostearate (Emulsifier) | 3 |
| Stearyl Alcohol (Emollient/Viscosity Builder) | 3 |
| Cremophor RH-40 (Emulsifier/Solubilizer) | 2 |
| Arlacel 165 (Emulsifier) | 2 |

Part C

| Component | % w/w |
| --- | --- |
| Optiphen MIT Plus (Preservative) | 0.2 |
| Isopropanol (Solvent) | 5 |
| Triethanolamine (pH neutralizer) | 0.3 |

Procedure

1. Add water into main vessel, turn on mixer. Slowly sprinkle Carbomer 940 into vessel while mixing. Mix until no visible lump and start to heat the vessel to 70 C.
2. Add rest ingredients in the Part A into the main vessel while keeping mixing and keep temperature at 70 C.
3. Add all ingredients in Part B into a separate vessel, heat to 70 C. Once it becomes clear at 70 C., add it into main vessel while mixing.
4. Mix 5 minutes at 70 C., then start to cool down the batch to room temperature.
5. Add all ingredients in Part C into a separate vessel, mix well and slowly add into main vessel at room temperature.
6. Mix for another 15-20 minutes until it's homogenous.

Example 2

Part A

| Component | % w/w |
| --- | --- |
| Water | 72.3 |
| Carbomer 940 (Thickener) | 0.7 |
| Guanidine HCl (Basement Membrane Disrupter/Chaotropic Agent) | 1 |
| Glycerin (Humectant) | 2 |
| Urea (Humectant) | 5 |
| Arginine HCl (Vaso-modulator/Vasodilator) | 0.5 |

Part B

| Component | % w/w |
| --- | --- |
| Oleic Acid (Emulsifier/Penetration Enhancer/Agent) | 3 |
| Glyceryl Monostearate (Emulsifier) | 3 |
| Stearyl Alcohol (Emollient/Viscosity Builder) | 3 |
| Cremophor RH-40 (Emulsifier/Solubilizer) | 2 |
| Arlacel 165 (Emulsifier) | 2 |

Part C

| Component | % w/w |
| --- | --- |
| Oleic Acid (Emulsifier/Penetration Enhancer/Agent) | 2 |
| Tolnaftate (Active Ingredient) | 1 |

Part D

| Component | % w/w |
| --- | --- |
| Optiphen MIT Plus (Preservative) | 0.2 |
| Dimethyl Sulfoxide (Solvent) | 2 |
| Triethanolamine (pH neutralizer) | 0.3 |

Procedure

1. Add water into main vessel, turn on mixer. Slowly sprinkle Carbomer 940 into vessel while mixing. Mix until no visible lump and start to heat the vessel to 70 C.
2. Add rest ingredients in the Part A into the main vessel while keeping mixing and keep temperature at 70 C.
3. Add all ingredients in Part B into a separate vessel, heat to 70 C. Once it becomes clear at 70 C., add it into main vessel while mixing.
4. Mix 5 minutes at 70 C., then start to cool down the batch to room temperature.
5. Mix all ingredients together in Part C in a separate vessel, then add it into main vessel at room temperature.

6. Add all ingredients in Part D into a separate vessel, mix well and slowly add into main vessel at room temperature.
7. Mix for another 15-20 minutes until it's homogenous.

Example 3

Part A

Formulation I. the following components were mixed together in the amounts indicated:

| Component | Amount % by weight | Type |
|---|---|---|
| Water | 83.795 | |
| Bromelain | 0.6 | Proteolytic Agent/Basement membrane disrupter |
| Tween 80 | 4.0 | Surfactant/Solubilizer |
| Alcohol SD-40 | 10.0 | Solvent/second penetration agent |
| Oleic Acid | 0.1 | Solubilizer/second penetration agent |
| Grapefruit Oil | 0.1 | Flavor |
| Peppermint Oil | 0.1 | Mucolytic Agent/first penetration agent |
| Papaverine HCl | 0.005 | Vasodilator |
| Caffeine | 1.0 | Active Pharmaceutical Ingredient |
| Methylparaben | 0.2 | Preservative |
| Potassium Hydroxide 10% Sol. | 0.1 | Neutralizer |

Example 4

Formulation II. the following components were mixed together in the amounts indicated:

| Component | Amount % by weight | Type |
|---|---|---|
| Water | 82.225 | |
| Poloxamer 407 | 1.0 | Surfactant |
| Bromelain | 1.0 | Proteolytic Agent/basement membrane disruptor |
| Cremophor RH 40 | 4.0 | Surfactant/Solubilizer |
| Alcohol SD-40 | 10.0 | Solvent/second penetration agent |
| Oleic Acid | 0.1 | Solubilizer/second penetration agent |
| Grapefruit Oil | 0.1 | Flavor |
| Peppermint Oil | 0.1 | Mucolytic Agent/first penetration agent |
| Papaverine HCl | 0.005 | Vasodilator |
| Lidocaine Hydrochloride | 1.0 | Active Pharmaceutical Ingredient |
| Methylparaben | 0.2 | Preservative |
| Potassium Hydroxide 10% Sol | 0.27 | Neutralizer |

Example 5

Experiment: Cannabidiol (CBD) Transmucosal Formulations

Abstract

To further reinforce the effectiveness of the present invention, the following formulations were made using the present invention (a first penetration agent, a second penetration agent, a basement membrane disrupter, a delivery package including an active agent and a vasodilator) with 3% by weight CBD as the active agent and 1% by weight of either pancreatin or Trypsin II, an enzyme, that acts as a basement membrane disrupter (Inventive Formulations (IF)), 0.015% peppermint oil as the first penetration agent, 0.005% arginine HCL as the vasodilator, and oleic acid as the solvent/second penetration agent. Franz cell analysis and a comparative analysis was conducted using CBD as an active agent. CBD is a very difficult molecule to penetrate mucosal tissue (Buccal pouch) as it is highly lipophilic and tends to get sequestered into mucosal tissue. As the results demonstrated, the present invention was able to achieve significant penetration through the EpiOral™ membrane that far exceeded the control. Note that the EpiOral™ buccal tissue, used in the Franz Cell test, consists of normal, human-derived oral epithelial cells used to determine the mucosal absorption potential of formulations in vitro. The Franz Cell data generated by this experiment provided sufficient passive penetration evidence regarding penetration speed and active drug quantities to be considered meaningful transmembrane and intra-membrane oral epithelial penetration.

Methodology

The permeation experiments were conducted with the EpiOral™ buccal tissue Kit (ORL-200), which was purchase from MatTek Corporation (Ashland, MA, USA). EpiOral™ assay medium (MatTek, Ashland, MA, USA) was pre-warmed to 37° ° C. 0.3 mL/well of EpiOral™ assay medium were pipetted into 24-well plate labelled as 1-hr equilibration. The EpiOral™ samples were transferred into the 1-hr equilibration plate containing the pre-warmed assay medium and placed in a 37° C., 5% CO2 incubator for 1 hour.

The 4 formulas tested consisted of one commercially available CBD tincture that is marketed as a sublingual/transmucosal product. This product consists of CBD dissolved in a medium-chain triglyceride oil. Three formulas consisted of one formula that with just the base without any enzyme. The other two formulas fall under the present invention and consisted of the base with trypsin and the base with pancreatin.

For comparing the performance of the sublingual/transmucosal commercial product and various formulations of the inventive formula, 0.4 mL donor solution was added in contact with the apical surface of the EpiOral™ buccal tissue after 1-hr equilibration. The EpiOral™ tissues were then transferred to a new 24-well plate containing assay medium and returned to the incubator. After the elapsed time point (1 hour) the tissue was moved to the next new plate for the next time point (i.e., 2, 3, 4, 5 and 24-hr) till the total elapsed time (24 hour). The receiver fluid was filtered and analyzed by HPLC to quantify the amount of Cannabidiol (CBD). The evaluation was conducted on 4-6 replicates for all products respectively.

Results and Conclusion

Figure 3:
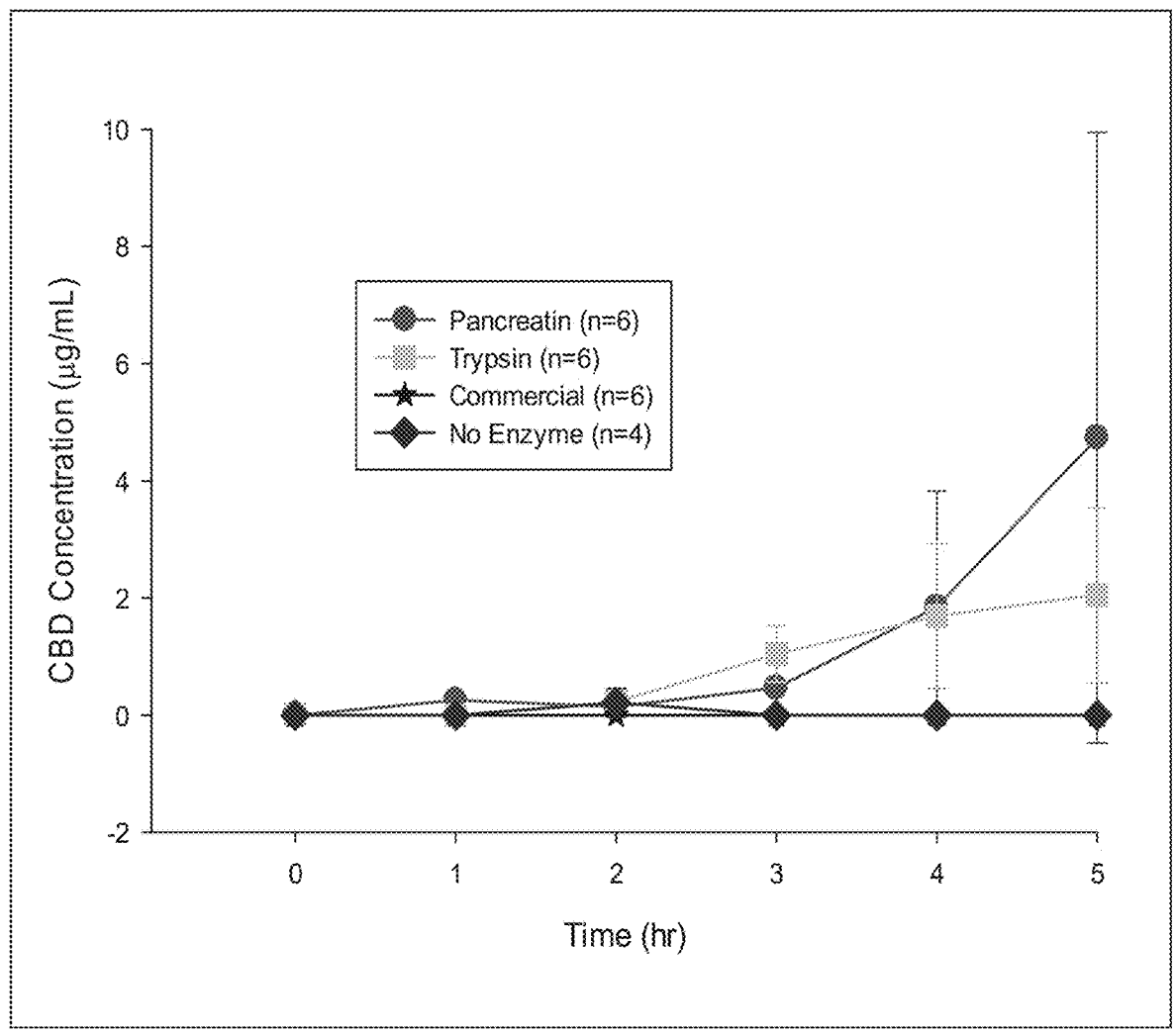
FIG. 3 is a line graph showing the CBD concentration in μg/mL over time (0-5 hours) for a formulation with no basement membrane disrupter, a commercial product, a formulation with trypsin as the basement membrane disrupter and a formulation with pancreatin as the basement membrane disrupter.
Figure 4:
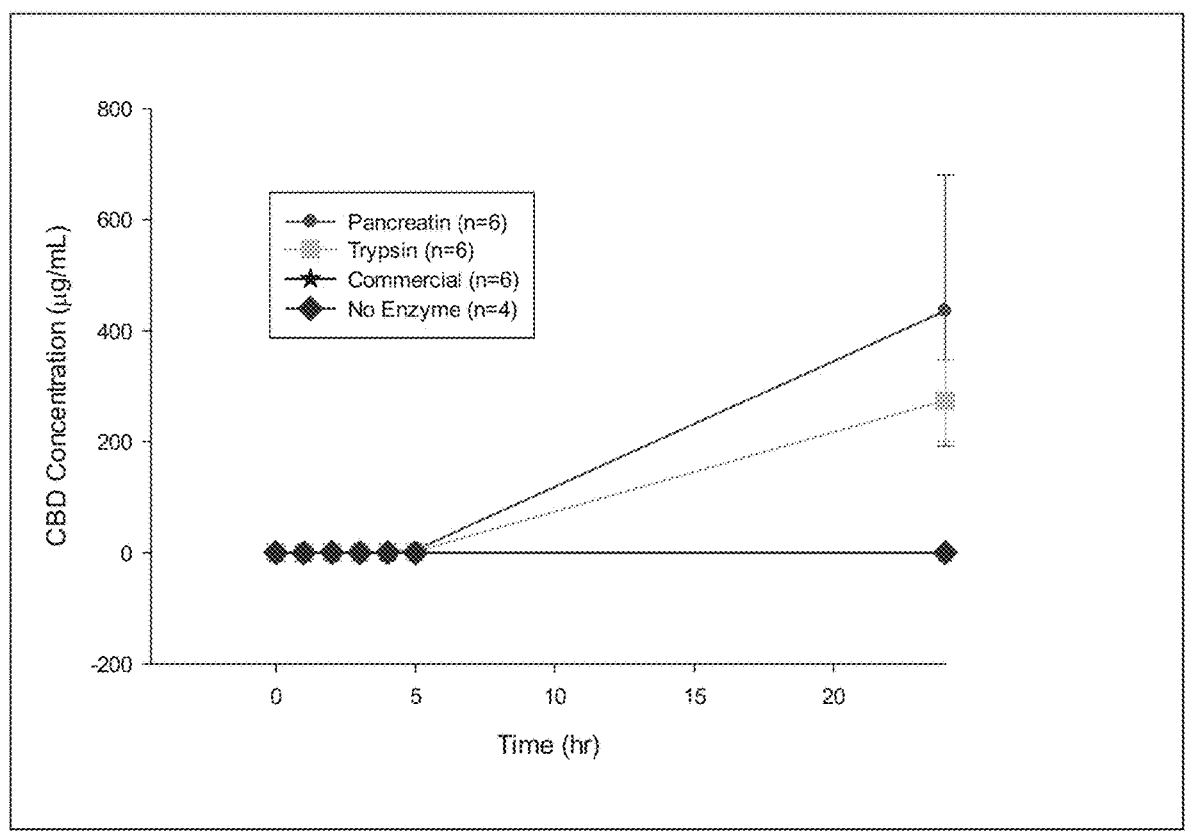
FIG. 4 is a line graph showing the CBD concentration in μg/mL over time (0-24 hours) for a formulation with no basement membrane disrupter, a commercial product, a formulation with trypsin as the basement membrane disrupter and a formulation with pancreatin as the basement membrane disrupter.

It is clear from the graphs shown in FIGS. 2-4 that both the Commercial Formula and the Inventive Formula without the enzymes had negligible penetration of the buccal tissue. By contrast, the two Inventive formulas that utilized trypsin and pancreatin respectively demonstrated a substantial increase in penetration at the three hour period (FIG. 2), five hour period (FIG. 3), and a 24 hour period (FIG. 4).

| Formulation | Replicate (n) | Mean of Amount in Solution (µg/mL) | | | | | |
|---|---|---|---|---|---|---|---|
| | | 1-hr | 2-hr | 3-hr | 4-hr | 5-hr | 24-hr |
| Pancreatin | 6 | 0.257 | 0.147 | 0.468 | 1.843 | 4.737 | 436.165 |
| Trypsin | 6 | 0 | 0.227 | 1.044 | 1.692 | 2.053 | 273.83 |
| No Enzyme | 4 | 0 | 0.215 | 0 | 0 | 0 | 10.218 |
| Commercial | 6 | 0 | 0 | 0 | 0 | 0 | 0 |

CONCLUSION

The CBD delivery data generated by the Franz Cell studies and data generated to show that the present invention has the capability of transporting difficult to penetrate molecules with different molecular sizes, partition coefficients and structures efficiently through mucosal tissue in meaningful time frames and in meaningful quantities. In particular, the CBD data shows the substantial penetration superiority of the present invention in both penetration speed and quantity over the control.

Additionally, the data showing the effectiveness of active agent delivery demonstrates that the present invention works surprisingly well considering that mucosa has been shown to be difficult to penetrate and provide effective administration of active agents.

The terms about, approximately, substantially, and their equivalents may be understood to include their ordinary or customary meaning. In addition, if not defined throughout the specification for the specific usage, these terms can be generally understood to represent values about but not equal to a specified value. For example, 1%, 0.9%, 0.8%, 0.7%, 0.6%, 0.5%, 0.4%, 0.3%, 0.2%, 0.1%, or 0.09% of a specified value.

The terms, "comprise," "include," "having" and/or plural forms of each are open ended and include the listed items and can include additional items that are not listed. The phrase "And/or" is open ended and includes one or more of the listed items and combinations of the listed items.

The relevant teachings of all the references, patents and/or patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A formulation for trans-epithelial membrane delivery of an active ingredient to a mammal; the formulation comprises:
   a) at least one first penetration agent, wherein the at least one first penetration agent is present in an amount ranging from 0.01% w/w to 2.0% w/w, wherein the at least one penetration agent is acetylcysteine, N-acetylcysteine, L-cysteine, ambroxol, bromhexine, carbocisteine, erdosteine, mecysteine, dornase alfa, althea extract, Marshmallow root, bromelain, thyme, salt water, eucalyptol, rosemary extract, cineole, peppermint, frankincense, oregano, bergamot, nutmeg, cypress, camphene, geranium, pelargonium sidoide, cinnamon, lemon, citrus, d-limonene, l-limonene, lavender, lemon grass, chamomile, basil or a combination thereof;
   b) at least one basement membrane disruptor, wherein the at least one basement membrane disruptor is present in an amount ranging from 0.2% w/w to 10% w/w, wherein the at least one basement membrane disruptor is a serine protease, a cysteine protease, a threonine protease, an aspartic protease, a glutamic protease, a lipase, a lactase, an ox bile extract, a phytase, a pancreatin, a pepsin, Chymotrypsin A, α-trypsin, and β-trypsin, papain, papaya, bromelain, pineapple, or a combination thereof;
   c) at least one vaso-modulator present in an amount ranging from 0.001% w/w to 15% w/w; and
   d) at least one active ingredient;
   wherein the formulation has a pH of between about 5.0 and about 6.5; and wherein the formulation allows for penetration of the active ingredient past the basement membrane.

2. The formulation of claim 1, wherein the formulation allows for penetration of the active ingredient to a smooth muscle.

3. The formulation of claim 1, wherein the body surface comprises skin, a mucosal membrane and a nail surface.

4. The formulation of claim 1, wherein the body surface comprises skin, oral mucosa, vaginal mucosa, anal mucosa, throat mucosa, nasal mucosa, ocular tissue, tracheal mucosa, lungs, fingernail surface, or toenail surface.

5. The formulation of claim 1, further comprising a second penetration agent that comprises a solvent, a lipophilic agent, a hydrophilic agent, or a combination thereof.

6. The formulation of claim 3, wherein the first penetration agent allows the basement membrane disruptor, the vaso-modulator, and the active ingredient to pass through a stratum corneum layer and an epidermis of the skin or a stratified squamous epithelial layer of the mucosal membrane.

7. The formulation of claim 5, wherein the second penetration agent comprises the solvent, wherein the solvent is selected from the group consisting of: one or more nonpolar solvents, one or more polar aprotic solvents, one or more polar protic solvents, one or more limonenes, one or more lipophilic agent, one or more fatty acid, and a combination thereof.

8. The formulation of claim 7, wherein the second penetration agent comprises one or more nonpolar solvents is selected from the group consisting of: carbon tetrachloride, benzene, diethyl ether, hexane, methylene chloride, toluene and a combination thereof.

9. The formulation of claim 7, wherein the second penetration agent comprises one or more polar aprotic solvents is selected from the group consisting of: propylene carbonate, acetone, ethyl acetate, acetonitrile, dimethylformamide, and a combination thereof.

10. The formulation of claim 7, wherein the second penetration agent comprises one or more polar protic solvents is selected from the group consisting of: water, methanol, isopropanol, acetic acid, methanol, ethanol, n-propanol, n-butanol and a combination thereof.

11. The formulation of claim 7, wherein the second penetration agent comprises one or more limonenes is selected from the group consisting of: D-limonene, L-Limonenes and a combination thereof.

12. The formulation of claim 7, wherein the second penetration agent comprises one or more fatty acids is selected from the group consisting of: linoleic acids, linolenic acids, oleic acids, stearic acids, myristic acids, phosphatidylcholine, and a combination thereof.

13. The formulation of claim 1, wherein the basement membrane disruptor denatures or cleaves one or more molecules of the basement membrane to allow for passage of the active ingredient.

14. The formulation of claim 1, wherein the basement membrane disruptor allows the vaso-modulator and the active ingredient pass through the basement membrane.

15. The formulation of claim 1, wherein the basement membrane disruptor further comprises one or more chaotropic agents.

16. The formulation of claim 1, wherein basement membrane disruptor is selected from the group consisting of: guanidine hydrochloride, a guanidine salt, guanidine analogs, guanidine conjugates; and a combination thereof.

17. The formulation of claim 1, wherein the vaso-modulator comprises a vasodilator.

18. The formulation of claim 17, wherein the vasodilator allows for the active ingredient to be delivered systemically or to local tissue.

19. The formulation of claim 17, wherein the vasodilator is selected from the group consisting of: amrinone, arginine, bamethan sulphate, bencyclane fumarate, benfurodil hemisuccinate, benzyl nicotinate, buflomedil hydrochloride, buphenine hydrochloride, butalamine hydrochloride, cetiedil citrate, ciclonicate, cinepazide maleate, cyclandelate, di isopropylammonium dichloroacetate, ethyl nicotinate, hepronicate, hexyl nicotinate, ifenprodil tartrate, inositol nicotinate, isoxsuprine hydrochloride, kallidinogenase, methyl nicotinate, naftidrofuryl oxalate, nicametate citrate, niceritrol, nicoboxil, nicofuranose, nicotinyl alcohol, nicotinyl alcohol tartrate, nitric oxide, nonivamide, oxpentifylline, papaverine, papaveroline, pentifylline, peroxynitrite, pinacidil, pipratecol, propentofyltine, raubasine, suloctidil, teasuprine, thymoxamine hydrochloride, tocopherol nicotinate, tolazoline, papaverine, xanthinol nicotinate, diazoxide, hydralazine, minoxidil, and sodium nitroprusside, clonidine, quanaberz, methyl dopa, alpha adrenoceptor, indoramin, phenoxybenzamine, phentolamine, prazosin, PDE-5 inhibitors, sildenafil, tadalafil, adrenergic neuron blocking agents, bedmidine, debrisoquine, guanethidine, ACE inhibitors, benazepril, captopril, cilazapril, enalapril, fosinopril, lisinopril, perindopril, quinapril, ramipril, ganglion blocking agents, pentolinium, trimetaphan, calcium channel blockers, amlodipine, diltiazem, felodipine, isradipine, nicardipine, nifedipine, nimodipine, verapamil, prostaglandins, prostacyclin, thrombuxane A2, leukotrienes, PGA, PGA1, PGA2, PGE1, PGE2, PGD, PGG, PGH, angiotensin II analogs, saralasin, nitroglycerin, labetalol, thrazide, isosorbide dinitrate, pentaerythritol tetranitrate, digitalis, hydralazine, diazoxide, sodium nitroprusside, and a combination thereof.

20. The formulation of claim 1, wherein the active ingredient is present in an amount ranging from about 0.001% w/w and about 30% w/w.

21. The formulation of claim 1, wherein the active ingredient is selected from the group consisting of: acetaminophen, acetohydoxamic acid, acetophenazine, acyclovir, albuterol, allopurinol, amiloride, amoxicillin, amphetamine, ampicillin, antisense polymers, atenolol, baclofen, beclomethasone, benfotiamine, betamethasone, budesonide, bumetanide, butorphanol, carbamazepine, carphenazine, celacoxhib, cefuroxime, cephradine, chloramphenicol, chlorothiazide, chlorzoxazone, cinoxacin, clorazepate, cloxacillin, cyclacillin, dapsone, dicloxacillin, diethylstilbestrol, dopamine, doxorubicin, erythropoietin, estradiol, fenoprofen, gabapentin, human growth hormone, hydralazine, hydrochlorothiazide, ibuprofen, indomethacin, insulin, isoproterenol, ketoprofen, levodopa, levothyroxine, meclofenamate, melphalan, metformin methyl salicylate, metronidazole, minoxidil, morphine, nadolol, nalidixic acid, naproxen, nomifensine, norfloxacin, oxaprozin, oxycontin, paramethasone, peptide fragments, perphenazine, phenylpropanolamine, pregabalin, probenecid, quinethazone, ritodrine, scopolamine, serotonin, sildenafil, tadalafil, terbutaline, terfenadine, tocainide, terbinafine, triamterene, riamterine, trimethoprim, valacyclovir, a sirtuin inhibitor, nicotinamide, AIII, coumarin, sirtinol, alpha-NAD, carbamido-NAD, trichostatin A, suramin sodium, apicidin, BML-210, BML-266, depudecin, HC Toxin, ITSA1, nullscript, phenylbutyrate, sodium, scriptaid, splitomicin, suberoyl bis-hydroxamic acid, a sirtuin activators, resveratrol, isonicotinamide, butein, luteolin, plant extract, hemp, nicotine, hemp derived compounds, terpenes, and a combination thereof.

22. The formulation of claim 1, further comprising a transpiration barrier, wherein the transpiration barrier includes at least one of a chemical barrier or a physical barrier.

23. A kit for transdermal delivery of an active ingredient to a mammal; the kit comprises
a) at least one first penetration agent, wherein the at least one penetration agent is present in an amount ranging from 0.01% w/w to 2.0% w/w, wherein the at least one penetration agent is acetylcysteine, N-acetylcysteine, L-cysteine, ambroxol, bromhexine, carbocisteine, erdosteine, mecysteine, dornase alfa, althea extract, Marshmallow root, bromelain, thyme, salt water, eucalyptol, rosemary extract, cineole, peppermint, frankincense, oregano, bergamot, nutmeg, cypress, camphene, geranium, pelargonium sidoide, cinnamon, lemon, citrus, d-limonene, 1-limonene, lavender, lemon grass, chamomile, basil or a combination thereof;
b) at least one basement membrane disruptor, wherein the at least one basement membrane disruptor is present in an amount ranging from 0.2% w/w to 10% w/w, wherein the at least one basement membrane disruptor is a serine protease, a cysteine protease, a threonine protease, an aspartic protease, a glutamic protease, a lipase, a lactase, an ox bile extract, a phytase, a pancreatin, a pepsin, Chymotrypsin A, α-trypsin, and β-trypsin, papain, papaya, bromelain, pineapple, or a combination thereof;
c) at least one vaso-modulator present in an amount ranging from 0.001% w/w to 15% w/w; and
d) at least one active ingredient;
wherein the kit creates a formulation that allows for penetration of the active ingredient to a smooth muscle, wherein the formulation has a pH of between about 5.0 and about 6.5; and
wherein the formulation allows for penetration of the active ingredient past the basement membrane.

24. The kit of claim 23, further comprising a set of written instructions for use, by or on said mammal.

* * * * *